(12) United States Patent
Patil et al.

(10) Patent No.: US 8,507,523 B2
(45) Date of Patent: Aug. 13, 2013

(54) THERAPEUTIC TETRAHYDROISOQUINOLINE-BASED COMPOSITIONS FOR CANCER THERAPY

(76) Inventors: Renukadevi Patil, Memphis, TN (US); Charles Ryan Yates, Collierville, TN (US); Duane D. Miller, Germantown, TN (US); Eldon E. Geisert, Germantown, TN (US)

( * ) Notice: Subject to any disclaimer, the term of this patent is extended or adjusted under 35 U.S.C. 154(b) by 1121 days.

(21) Appl. No.: 11/944,295

(22) Filed: Nov. 21, 2007

(65) Prior Publication Data

US 2008/0146597 A1   Jun. 19, 2008

Related U.S. Application Data

(60) Provisional application No. 60/866,606, filed on Nov. 21, 2006.

(51) Int. Cl.
*C07D 401/10* (2006.01)
*A61K 31/4725* (2006.01)

(52) U.S. Cl.
USPC ............ 514/307; 546/147; 546/148; 546/150

(58) Field of Classification Search
USPC ......... 544/333; 546/147, 148, 150; 514/256, 514/307
See application file for complete search history.

(56) References Cited

FOREIGN PATENT DOCUMENTS

WO   WO 03/077874   *   9/2003

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Akasu et al., CAPLUS Abstract 112:42617 (1990).*

* cited by examiner

*Primary Examiner* — Deepak Rao

(57) ABSTRACT

Disclosed are therapeutic tetrahydroisoquinoline compositions for the treatment of cancer, these compositions having selectivity for cancer cells while demonstrating few, if any, deleterious side effects on normal cells.

10 Claims, 4 Drawing Sheets

THERAPEUTIC TETRAHYDROISOQUINOLINE-BASED COMPOSITIONS FOR CANCER THERAPY

CROSS-REFERENCE TO RELATED APPLICATIONS

This application claims the benefit of priority of U.S. Provisional Patent Application No. 60/866,606, filed Nov. 21, 2006.

FIELD OF THE INVENTION

This invention relates to compositions and methods of use of those compositions for cancer therapy. More specifically, the invention relates to synthesized tetrahydroisoquinoline-based compositions for cancer treatment.

BACKGROUND OF THE INVENTION

According to the American Cancer Society, there were approximately 1,372,910 new cancer cases in 2005, with an additional 1 million cases of basal and squamous cell skin cancers in that same period. The five-year survival rate for cancer diagnosed between 1995 and 2000 was 64%, primarily due to improved methods of treatment and early detection. Still, over one-third of cancer patients were not expected to survive for five years, and a significant percentage of those who would survive for five years would have a recurrence of cancer, leading to a decreased survival rate at ten years and beyond.

Most academic research institutions and many pharmaceutical companies around the world have multiple oncology research programs focused on the development of new cancer-fighting agents, and the number of new compounds synthesized each year is considerable. There still remains a need, however, for agents that combat various forms of cancer and there is a special need for agents that are selective for cancer cells while sparing normal cells from damage.

SUMMARY OF THE INVENTION

The present invention relates to compositions of Formula (I)

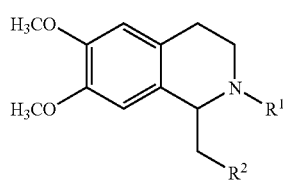

(I)

wherein $R^1$ is H, $H_2Cl$, $CH_3$, or —$COOC(CH_3)_3$; $R^2$ is

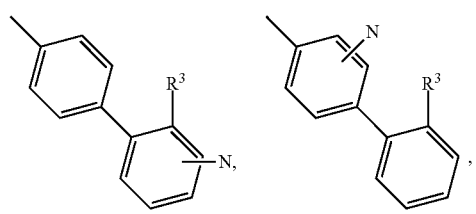

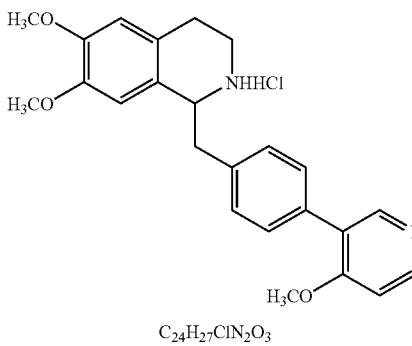

$R^3$ and $R^4$ are each independently H, —$OCH_3$, —$CF_3$, —$NHSO_2CH_3$, —$NHCOCH_3$, —$SO_2CH_3$, —$N(CH_3)_2$, —CN, —$NO_2$, —$NH_2$, —$CO_2CH_3$, —$OCF_3$, —$CH_3$, F, Cl, Br, or I.

The invention also relates to methods of use of compounds of Formula (I) for the treatment of cancer. In one embodiment, the method is a method of treating glioma with one or more compounds as described herein.

In one embodiment, a composition for the treatment of cancer is

Compositions are also provided as in Formula (II)

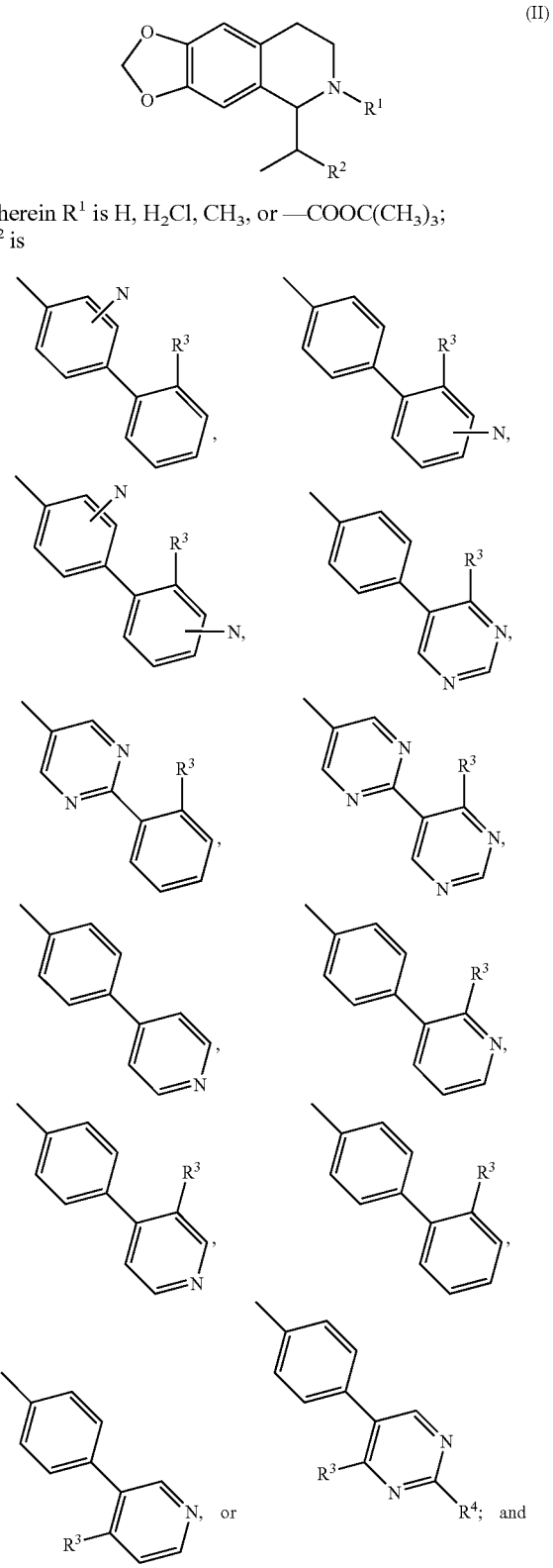

wherein R¹ is H, H₂Cl, CH₃, or —COOC(CH₃)₃;
R² is

R³ and R⁴ are each independently H, —OCH₃, —CF₃, —NHSO₂CH₃, —NHCOCH₃, —SO₂CH₃, —N(CH₃)₂, —CN, —NO₂, —NH₂, —CO₂CH₃, —OCF₃, —CH₃, F, Cl, Br, or I.

DETAILED DESCRIPTION

Figure 1:
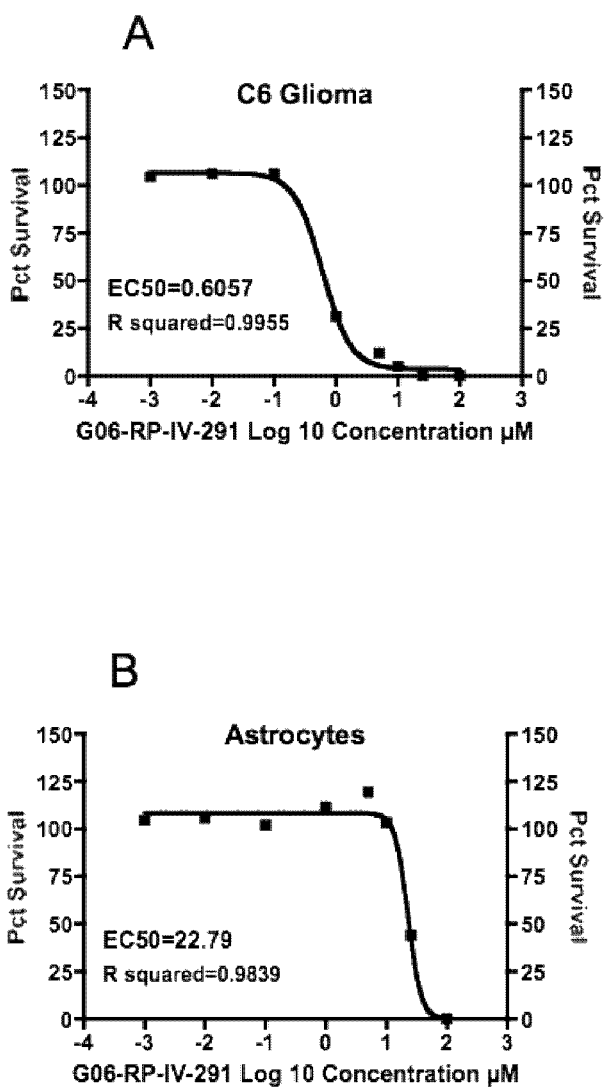
FIG. 1 provides dose/response curves for 6,7-Dimethoxy-1-[4-(4-methoxypyridin-3-yl)benzyl]-1,2,3,4-tetrahydroisoquinolinehydrochloride (EDL-291) for cultured normal rat brain astrocytes and C6 glioma are illustrated. The percentage of surviving cells is plotted against the concentration of the drug. In A the percentage of cells surviving after 4 days of treatment with different concentrations of EDL-291 is shown. Notice that the C6 glioma (EC50=0.6 µM) is more sensitive to EDL-291 than are astrocytes (EC50=26 µM).

The inventors have synthesized compositions with selective cytotoxicity for cancer cells. Compositions described by the present invention include substituted tetrahydroisoquinoline compounds as in Formula (I):

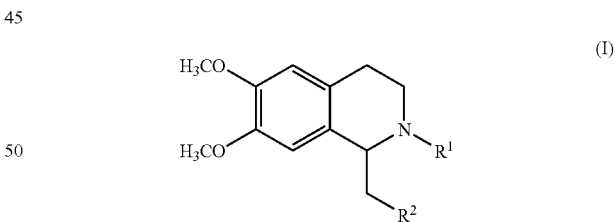

wherein R¹ is H, H₂Cl, CH₃, or —COOC(CH₃)₃;
R² is

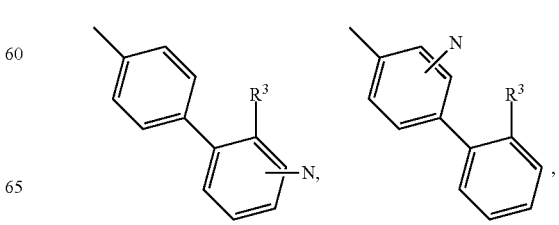

-continued

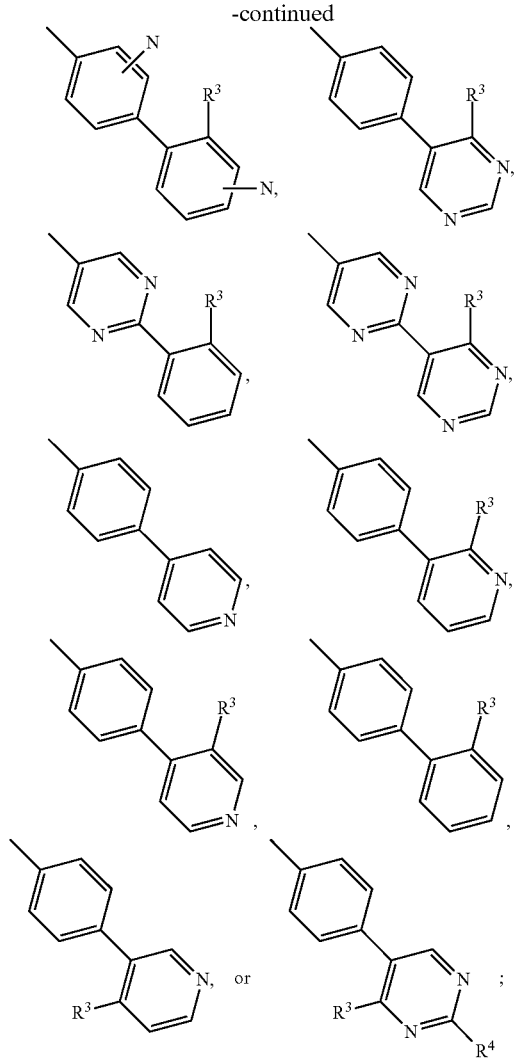

$R^3$ and $R^4$ are each independently —H, —OCH$_3$, —CF$_3$, —NHSO$_2$CH$_3$, —NHCOCH$_3$, —SO$_2$CH$_3$, —N(CH$_3$)$_2$, —CN, —NO$_2$, —NH$_2$, —CO$_2$CH$_3$, —OCF$_3$, —CH$_3$, —F, —Cl, —Br, or —I.

An especially effective composition of the invention that has been shown by the inventors to destroy tumors within a matter of days, while exhibiting no detectable signs of toxicity for normal cells, is

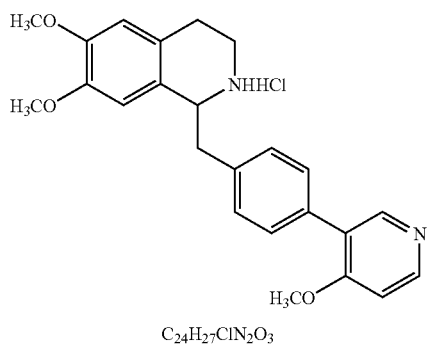

C$_{24}$H$_{27}$ClN$_2$O$_3$

Compositions of the invention are also described by Formula (II)

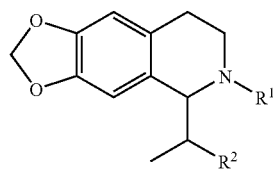

wherein $R^1$ is H, H$_2$Cl, —CH$_3$, or —COOC(CH$_3$)$_3$;

$R^2$ is

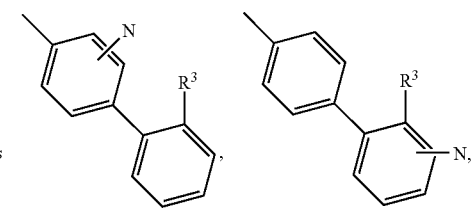

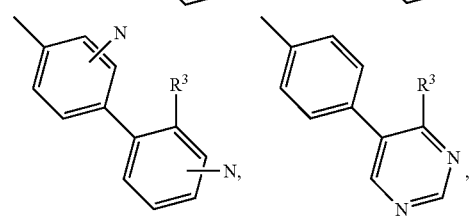

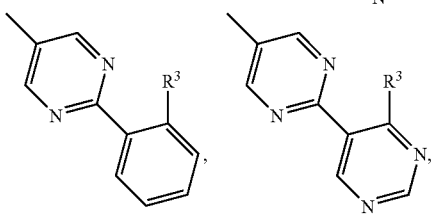

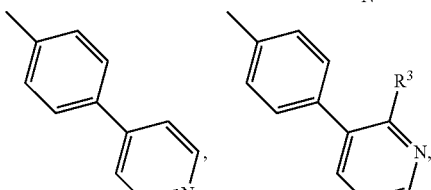

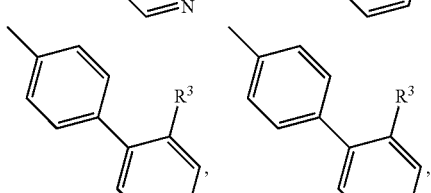

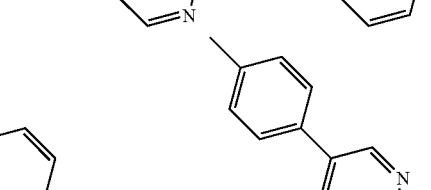

$R^3$ and $R^4$ are each independently H, —OCH$_3$, —CF$_3$, —NHSO$_2$CH$_3$, —NHCOCH$_3$, —SO$_2$CH$_3$, —N(CH$_3$)$_2$, —CN, —NO$_2$, —NH$_2$, —CO$_2$CH$_3$, —OCF$_3$, —CH$_3$, F, Cl, Br, or I.

Compositions of the invention may also include pharmacologically acceptable salts thereof. Compositions of the invention are provided for the treatment of a variety of forms of cancer in human and animals. For example, compounds of the invention have been found to be highly effective for the treatment of glioma, retinoblastoma, and other forms of cancer. Therapeutically effective amounts of the inventive compositions may vary among individuals, depending upon the type of cancer, the body mass of the individual, the age of the individual, etc., as do all pharmaceutical compositions. To those of skill in the art of cancer therapy and pharmacology, however, therapeutically effective amounts of the compositions may readily be determined based upon the disclosure by the inventors herein. Useful dosages of the compounds of formula (I) may be determined by comparing their in vitro activity, and in vivo activity in animal models. Methods for the extrapolation of effective dosages in mice, and other animals, to humans are known to the art, such as in, for example, U.S. Pat. No. 4,938,949.

Compositions of the invention may be administered to a human or an animal subject by the variety of means by which pharmaceuticals for oncology are known to be administered to patients, including, for example, intravenous administration, intraperitoneal administration, administration via a pharmaceutical reservoir from which the composition may be provided via a pump or via encapsulation or associated with modified release compositions, and other means known to those of skill in the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art such as, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula (I) can be formulated as pharmaceutical compositions that may be administered to a mammalian subject such as a human patient via a variety of forms adapted to the chosen route(s) of administration, such as by oral, parenteral, intravenous, intramuscular, topical or subcutaneous routes. The present compounds may be systemically or orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms may be achieved by various antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present compounds may be applied in pure form, e.g., when they are liquids. However, it may generally be desirable to administer them to the skin as compositions or formulations, in combination with a dermatologically acceptable carrier, which may be a solid or a liquid. Useful solid carriers may include, for example, finely divided solids such as talc, clay, microcrystalline cellulose, silica, alumina. Useful liquid carriers may include, for example, water, dimethyl sulfoxide (DMSO), alcohols or glycols or water-alcohol/glycol blends, in which the present compounds can be dissolved or dispersed at effective levels, optionally with the aid of non-toxic surfactant. Thickeners such as synthetic polymers, fatty acids, fatty acid salts and esters, fatty alcohols, modified celluloses or modified mineral materials may also be employed with liquid carriers to form, for example, spreadable pastes, gels, ointments, or soaps for application directly to the skin of the user.

In a method of treating cancer using compositions described herein, administration may be provided according to a schedule of administration determined by the patient's physician, and may be at relatively regularly-spaced intervals such as daily, every other day, twice daily, etc. Compounds of the invention may be beneficial for the treatment of glioma, retinoblastoma, and a variety of other cancers, including, but not limited to, cancers arising within the nervous system, respiratory system, gastrointestinal system, cardiovascular system, cancers of the lung, liver, intestines, skin cancers such as melanomas, breast cancer, and prostate cancer.

The synthesis of 6,7-dimethoxy-1-(4-pyridin-4-ylbenzyl)-3,4-dihydro-1H-isoquinoline-2-carboxylic acid tert-butyl ester 3 and 6,7-dimethoxy-1-(4-pyridin-4-ylbenzyl)-1,2,3,4-tetrahydroisoquinoline hydrochloride salt 4 is shown in scheme-1. Reaction of 1-(4-bromobenzyl)-6,7-dimethoxy-3,4-dihydro-1H-isoquinoline-2-carboxylic acid tert-butyl ester 1 with pyridine-4-boronic acid 2 in the presence of Palladium (II) acetate, triphenylphosphine, and $Na_2CO_3$ in anhydrous isopropanol yielded the compound 3 which was treated with 2 M HCl solution in diethylether to give compound 4 (Scheme-1).

6,7-Dimethoxy-1-[4-(2-methoxypyridin-3-yl)benzyl]-3,4-dihydro-1H-isoquinoline-2-carboxylic acid tert-butyl ester 6 was synthesized by the Suzuki coupling of 1-(4-bromobenzyl)-6,7-dimethoxy-3,4-dihydro-1H-isoquinoline-2-carboxylic acid tert-butyl ester 1 with 2-methoxypyridine-3-boronic acid 5 using Palladium(II) acetate, triphenylphosphine, and $Na_2CO_3$ in anhydrous isopropanol. Compound 6 was treated with 2 M HCl solution in diethylether to get 6,7-dimethoxy-1-[4-(2-methoxypyridin-3-yl)benzyl]-1,2,3,4-tetrahydroisoquinoline hydrochloride salt 7. Reaction of 7 with formaldehyde in the presence of sodium cyanoborohydride, and zinc chloride furnished 6,7-dimethoxy-1-[4-(2-methoxypyridin-3-yl)benzyl]-2-methyl-1,2,3,4-tetrahydro-isoquinoline 8 which was treated with 2 M HCl solution in diethylether to obtain 6,7-dimethoxy-1-[4-(2-methoxypyridin-3-yl)benzyl]-2-methyl-1,2,3,4-tetrahydro-isoquinolinehydrochloride 9 (Scheme-2).

The synthesis of 6,7-dimethoxy-1-[4-(3-methoxypyridin-4-yl)benzyl]-1,2,3,4-tetrahydroisoquinoline hydrochloride salt 12 is shown in Scheme 3. Reaction of 1-(4-bromobenzyl)-6,7-dimethoxy-3,4-dihydro-1H-isoquinoline-2-carboxylic acid tert-butyl ester 1 with 3-methoxypyridine-4-boronic acid 10 in the presence of Palladium(II) acetate, triphenylphosphine, and $Na_2CO_3$ yielded 6,7-dimethoxy-1-[4-(3-methoxypyridin-4-yl)benzyl]-3,4-dihydro-1H-isoquinoline-2-carboxylic acid tert-butyl ester 11 which was then treated with 2 M HCl solution in diethylether to get compound 12. N-[4'-(6,7-dimethoxy-1,2,3,4-tetrahydroisoquinolin-1-ylmethyl)biphenyl-2-yl]-methanesulfonamide hydrochloride salt 15 was prepared by the reaction of 1-(2'-Methanesulfonyl-aminobiphenyl-4-ylmethyl)-6,7-dimethoxy-3,4-dihydro-1H-isoquinoline-2-carboxylic acid tert-butyl ester 14 with 2 M HCl solution in diethylether. Compound 14 was obtained by the Suzuki coupling of compound 1 with (2-methylsulfonylaminophenyl)-boronic acid 13 using Palladium(II) acetate, triphenylphosphine, and $Na_2CO_3$ in isopropanol (scheme-4).

1-(2'-Acetylaminobiphenyl-4-ylmethyl)-6,7-dimethoxy-3,4-dihydro-1H-isoquinoline-2-carboxylic acid tert-butyl ester 17 was synthesized by the Suzuki coupling of 1-(4-bromobenzyl)-6,7-dimethoxy-3,4-dihydro-1H-isoquinoline-2-carboxylic acid tert-butyl ester 1 with 2-acethylaminophenylboronic acid 16 using Palladium(II) acetate, triphenylphosphine, and $Na_2CO_3$ in anhydrous isopropanol. Reaction of compound 17 with 2 M HCl solution in diethylether yielded N-[4'-(6,7-dimethoxy-1,2,3,4-tetrahydro-isoquinolin-1-ylmethyl)-biphenyl-2-yl]acetamide hydrochloride salt 18 (Scheme-5).

The synthesis of 6,7-dimethoxy-1-[4-(4-methoxypyridin-3-yl)benzyl]-2-methyl-1,2,3,4-tetrahydroisoquinoline hydrochloride 23 is shown in Scheme 6. 6,7-Dimethoxy-1-[4-(4-methoxypyridin-3-yl)benzyl]-3,4-dihydro-1H-isoquinoline-2-carboxylic acid tert-butyl ester 20 was prepared by the reaction of 1-(4-bromobenzyl)-6,7-dimethoxy-3,4-dihydro-1H-isoquinoline-2-carboxylic acid tert-butyl ester 1 with 4-methoxypyridine-3-boronic acid 19 in the presence of Palladium(II) acetate, triphenylphosphine, and $Na_2CO_3$ in anhydrous isopropanol. Reaction of compound 20 with 2 M HCl solution in diethylether gave 6,7-dimethoxy-1-[4-(4-methoxypyridin-3-yl)benzyl]-1,2,3,4-tetrahydroisoquinolinehydrochloride salt 21. Reaction of 21 with formaldehyde, sodium cyanoborohydride, and zinc chloride in methanol furnished 6,7-dimethoxy-1-[4-(4-methoxypyridin-3-yl)benzyl]-2-methyl-1,2,3,4-tetrahydroisoquinoline 22 which was then reacted with 2 M HCl solution in diethylether to yield the compound 23.

1-[4-(2,4-Dimethoxypyrimidin-5-yl)benzyl]-6,7-dimethoxy-3,4-dihydro-1H-isoquinoline-2-carboxylic acid tert-butyl ester 25 was synthesized by the Suzuki coupling of 1-(4-bromobenzyl)-6,7-dimethoxy-3,4-dihydro-1H-isoquinoline-2-carboxylic acid tert-butyl ester 1 with 2,4-dimethoxypyrimidine-5-boronic acid 24 using Palladium(II) acetate, triphenylphosphine, and $Na_2CO_3$. Reaction of compound 25 with 2 M HCl solution in diethylether yielded 1-[4-(2,4-dimethoxypyrimidin-5-yl)benzyl]-6,7-dimethoxy-1,2,3,4-tetrahydroisoquinoline hydrochloride salt 26 (Scheme-7).

The synthesis of 6,7-dimethoxy-1-(4-pyrimidin-5-ylbenzyl)-1,2,3,4-tetrahydro-isoquinoline hydrochloride 29 is shown in Scheme 8. 6,7-Dimethoxy-1-(4-pyrimidin-5-ylbenzyl)-3,4-dihydro-1H-isoquinoline-2-carboxylic acid tert-butyl ester 28 was synthesized by the reaction of 1-(4-bromobenzyl)-6,7-dimethoxy-3,4-dihydro-1H-isoquinoline-2-carboxylic acid tert-butyl ester 1 with pyrimidine-5-boronic acid 27 using Palladium(II) acetate, triphenylphosphine, and $Na_2CO_3$ in anhydrous isopropanol. Compound 28 was treated with 2 M HCl solution in diethylether to obtain the compound 29.

1-[4-(2-Chloropyridin-3-yl)benzyl]-6,7-dimethoxy-1,2,3,4-tetrahydroisoquinoline hydrochloride salt 32 was synthesized by the reaction of 1-[4-(2-chloropyridin-3-yl)benzyl]-6,7-dimethoxy-3,4-dihydro-1H-isoquinoline-2-carboxylic acid tert-butyl ester 31 with 2 M HCl solution in diethylether. Compound 31 was prepared by the Suzuki coupling of 1-(4-bromobenzyl)-6,7-dimethoxy-3,4-dihydro-1H-isoquinoline-2-carboxylic acid tert-butyl ester 1 with 2-chloropyridine-3-boronic acid 30 in the presence of Palladium(II) acetate, triphenylphosphine, and $Na_2CO_3$ in anhydrous isopropanol (Scheme-9).

All the reagents and solvents were purchased from Aldrich, Frontier Scientific Inc., Combi-Blocks Inc., synthonix, and used without further purification. The reactions were performed under nitrogen atmosphere. Proton NMR spectra were recorded on a Bruker ARX 300 spectrometer (300 MHz) using DMSO-$d_6$, and spectral data were consistent with assigned structures. Chemical shift values were reported as parts per million (δ), coupling constants (J) are given in Hz, and splitting patterns are designated as follows: s, singlet; d, doublet; t, triplet; q, quartet; m, multiplet. Mass spectra were collected on a Brucker ESQUIRE electrospray/ion trap instrument in the positive and negative modes. Routine thin-layer chromatography (TLC) was performed on silica gel plates (Analtech, Inc., 250 microns). Flash chromatography was conducted on silica gel (Merck, grade 60, 230-400 mesh).

General Procedure for the Preparation of Compounds 3, 6, 11, 14, 17, 20, 25, 28, and 31:

A mixture of 1-(4-bromobenzyl)-6,7-dimethoxy-3,4-dihydro-1H-isoquinoline-2-carboxylic acid tert-butyl ester 1 (1 equiv.), Palladium(II)acetate (4 mol %), and triphenylphosphine (8 mol %) in anhydrous isopropanol was stirred under dry conditions at room temperature for 30 min. To this mixture, substituted pyridine/pyrimidine/phenylboronic acid (2 equiv.), and $Na_2CO_3$ (4 equiv.) were added successively, and the mixture was refluxed for 16 h. The solvent was concentrated under reduced pressure, the residue was partitioned between ethyl acetate, and saturated $NaHCO_3$ aqueous solution. Two layers were separated, and the aqueous layer was extracted with ethyl acetate. The combined organic layers were washed with water followed by brine, and dried over anhydrous $Na_2SO_4$. The solvents were removed under reduced pressure, and the crude residue was purified by flash column chromatography.

General Procedure for the Preparation of Compounds 4, 7, 12, 15, 18, 21, 26, 29, and 32:

2 M HCl solution in diethylether (20 equiv.) was added to a solution of 6,7-dimethoxy-1-[4-substituted benzyl]-3,4-dihydro-1H-isoquinoline-2-carboxylic acid tert-butyl ester (1 equiv.) in diethyl ether, and the reaction mixture was stirred over night. Filtered the mixture, the residue was washed with ether, and air dried. The crude residue was crystallized from methanol-ether to get 6,7-dimethoxy-1-[4-substituted benzyl]-1,2,3,4-tetrahydroisoquinoline hydrochloride salt.

General Procedure for the Preparation of Compounds 8 & 22:

Sodium cyanoborohydride (2 equiv.) and zinc chloride (1 equiv.) in methanol were added to a stirred mixture of 6,7-dimethoxy-1-[4-substituted pyridinbenzyl]-1,2,3,4-tetrahydroisoquinoline hydrochloride (1 equiv.) and formaldehyde (10 equiv. 37% solution in water) in methanol at room temperature. The reaction mixture was stirred overnight at the same temperature, concentrated under reduced pressure, the residue was treated with 1N HCl solution in water, and extracted with ethyl acetate. The organic phase was washed with water, and dried over anhydrous $Na_2SO_4$. The Solvent was evaporated under reduced pressure, and $CHCl_3$ was added and again evaporated under reduced pressure to afford 6,7-dimethoxy-1-[4-substituted pyridinbenzyl]-2-methyl-1,2,3,4-tetrahydroisoquinoline as oily mass which was used for further step without any purification.

General Procedure for the Preparation of Compounds 9 & 23:

2 M HCl solution in diethylether (20 equiv.) was added to a solution of 6,7-dimethoxy-1-[4-substituted pyridinbenzyl]-2-methyl-1,2,3,4-tetrahydroisoquinoline (1 equiv.) in diethyl ether at 0° C., the reaction mixture was warmed to room temperature and stirred over night. Filtered the reaction mixture, the residue was washed with ether, and air dried. The crude residue was crystallized from methanol-ether to yield 6,7-dimethoxy-1-[4-substituted pyridinbenzyl]-2-methyl-1,2,3,4-tetrahydroisoquinoline hydrochloride salt.

6,7-Dimethoxy-1-(4-pyridin-4-yl-benzyl)-3,4-dihydro-1H-isoquinoline-2-carboxylic acid tert-butyl ester (3)

Ethylacetate-hexane (20:80 to 90:10 v/v) was used as eluent for flash column chromatography (50%). MS (ES+) m/z 483 $(M+Na)^+$.

6,7-Dimethoxy-1-(4-pyridin-4-ylbenzyl)-1,2,3,4-tetrahydroisoquinoline hydrochloride salt (4)

The product was obtained in 70% yield as yellow colored powder. $^1$H NMR (300 MHz, DMSO-d6) δ 9.35 (bs, 2H, —$NH_2$), 8.87 (d, J=5.7 Hz, 2H, ArH), 8.23 (s, 2H, ArH), 8.02 (d, J=8.1 Hz, 2H, ArH), 7.60 (d, J=8.1 Hz, 2H, ArH), 6.81 (s, 1H, ArH), 6.53 (s, 1H, ArH), 5.76 (s, 1H, —CH—), 3.80 (s, 3H, —$OCH_3$), 3.74 (s, 3H, —$OCH_3$), 3.48-3.30 (m, 4H, 2*—$CH_2$), 3.05-2.88 (m, 2H, —$CH_2$). MS (ES+) m/z 361 $[M-(HCl)+H]^+$.

6,7-Dimethoxy-1-[4-(2-methoxypyridin-3-yl)benzyl]-3,4-dihydro-1H-isoquinoline-2-carboxylic acid tert-butyl ester (6)

Chloroform-methanol (100:0 to 98.2:0.2 v/v) was used as eluent for flash column chromatography (67%). In the NMR spectrum, two sets of peaks were appeared in the ratio of 1:0.3. $^1$H NMR (300 MHz, DMSO-d6) δ 8.16 (s, 1H, ArH), 7.69-7.66 (m, 1H, ArH), 7.48-7.46 (m, 3H, ArH), 7.32-7.22 (m, 3H, ArH), 7.09-7.08 (m, 1H, ArH), 6.84 (s, 1H, ArH), 6.72 (s, 1H, ArH), 6.59 (s, 1H, ArH), 5.23 (bs, 0.3H, —CH—), 5.13-5.10 (m, 1H, —CH—), 3.86 (d, J=3.3 Hz, 4H, —$OCH_3$), 3.72 (s, 7H, —$OCH_3$), 3.62 (s, 1H, —$OCH_3$), 3.26-2.93 (m, 5H, —$CH_2$), 2.78-2.59 (m, 3H, —$CH_2$), 1.32 [s, 3H, —$C(CH_3)_3$], 1.12 [s, 9H, —$C(CH_3)_3$]. MS (ES+) m/z 513 $(M+Na)^+$.

6,7-Dimethoxy-1-[4-(2-methoxypyridin-3-yl)benzyl]-1,2,3,4-tetrahydroisoquinoline hydrochloride salt (7)

The product was obtained in 51% yield as yellow colored powder. $^1$H NMR (300 MHz, DMSO-d6) δ 9.36 (d, J=21.6 Hz, 2H, —$NH_2$), 8.18 (d, J=4.8 Hz, 1H, ArH), 7.74 (d, J=7.5 Hz, 1H, ArH), 7.57 (d, J=7.2 Hz, 2H, ArH), 7.42 (d, J=7.5 Hz, 2H, ArH), 7.13-7.09 (m, 1H, ArH), 6.80 (s, 1H, ArH), 6.41 (s, 1H, ArH), 4.78 (s, 1H, —CH—), 3.88 (s, 3H, —$OCH_3$), 3.73 (s, 3H, —$OCH_3$), 3.51 (s, 3H, —$OCH_3$), 3.42-3.32 (m, 4H, 2*—$CH_2$), 2.99-2.89 (m, 2H, —$CH_2$). MS (ES+) m/z 391 $[M-(HCl)+H]^+$.

6,7-Dimethoxy-1-[4-(2-methoxypyridin-3-yl)benzyl]-2-methyl-1,2,3,4-tetrahydroisoquinolinehydrochloride (9)

The product was obtained as yellow powder. $^1$H NMR (300 MHz, DMSO-$d_6$) δ 11.00 (s, 1H, —NH), 8.17 (s, 1H, ArH), 7.70 (s, 1H, ArH), 7.57-7.47 (m, 2H, ArH), 7.31-7.15 (m, 2H, ArH), 7.09 (s, 1H, ArH), 6.83 (s, 1H, ArH), 5.72 (s, 1H, ArH), 4.64 (s, 1H, —CH—), 3.87 (s, 3H, —$OCH_3$), 3.80 (s, 6H, 2*—$OCH_3$), 3.72 (s, 3H, —$NCH_3$), 3.14-2.91 (m, 4H, 2*—$CH_2$), 2.89-2.75 (m, 2H, —$CH_2$). MS (ES+) m/z 406 $[M-(HCl)+H]^+$.

6,7-Dimethoxy-1-[4-(3-methoxypyridin-4-yl)benzyl]-3,4-dihydro-1H-isoquinoline-2-carboxylic acid tert-butyl ester (11)

Ethylacetate-hexane (20:80 to 90:10 v/v) was used as eluent for flash column chromatography (58%). In the NMR spectrum, two sets of peaks were appeared in the ratio of 1:0.3. $^1$H NMR (300 MHz, DMSO-d6) δ 8.45 (s, 1H, ArH), 8.23 (d, J=4.8 Hz, 1H, ArH), 7.52-7.46 (m, 3H, ArH), 7.35-7.24 (m, 4H, ArH), 6.85 (s, 1H, ArH), 6.71 (s, 1H, ArH), 6.61 (s, 1H, ArH), 5.27-5.18 (m, 0.3H, —CH—), 5.16-5.07 (m, 1H, —CH—), 3.88 (s, 4H, —OCH$_3$), 3.72 (s, 7H, —OCH$_3$), 3.62 (s, 1H, —OCH$_3$), 3.25-2.93 (m, 5H, —CH$_2$), 2.77-2.63 (m, 3H, —CH$_2$), 1.31 [s, 3H, —C(CH$_3$)$_3$], 1.10 [s, 9H, —C(CH$_3$)$_3$]. MS (ES+) m/z 513 (M+Na)$^+$.

6,7-Dimethoxy-1-[4-(3-methoxypyridin-4-yl)benzyl]-1,2,3,4-tetrahydroisoquinoline hydrochloride salt (12)

The product was obtained in 71% yield as yellow colored powder. $^1$H NMR (300 MHz, DMSO-d6) δ 9.32 (d, J=29.4 Hz, 2H, —NH$_2$), 8.68 (s, 1H, ArH), 8.54 (s, 1H, ArH), 7.76 (s, 1H, ArH), 7.69 (d, J=7.8 Hz, 2H, ArH), 7.50 (d, J=8.1 Hz, 2H, ArH), 6.81 (s, 1H, ArH), 6.41 (s, 1H, ArH), 4.74 (s, 1H, —CH—), 3.98 (s, 3H, —OCH$_3$), 3.74 (s, 3H, —OCH$_3$), 3.50 (s, 3H, —OCH$_3$), 3.39-3.32 (m, 4H, 2*—CH$_2$), 3.04-2.99 (m, 2H, —CH$_2$). MS (ES+) m/z 391 [M-(HCl)+H]$^+$.

1-(2'-Methanesulfonylaminobiphenyl-4-ylmethyl)-6,7-dimethoxy-3,4-dihydro-1H-isoquinoline-2-carboxylic acid tert-butyl ester (14)

Ethylacetate-hexane (20:80 to 60:40 v/v) was used as eluent for flash column chromatography (58%). In the NMR spectrum, two sets of peaks were appeared in the ratio of 1:0.5. MS (ES+) m/z 575 (M+Na)$^+$.

N-[4'-(6,7-Dimethoxy-1,2,3,4-tetrahydroisoquinolin-1-ylmethyl)-biphenyl-2-yl]-methanesulfonamide hydrochloride salt (15)

The product was obtained in 52% yield as yellow colored powder. $^1$H NMR (300 MHz, DMSO-d$_6$) δ 9.35 (s, 1H, —NH$_2$), 9.13 (s, 1H, —NH$_2$), 8.89 (d, J=10.5 Hz, 1H, —NH), 7.51-7.31 (m, 8H, ArH), 6.79 (d, J=10.2 Hz, 1H, ArH), 6.52 (d, J=10.5 Hz, 1H, ArH), 4.67 (s, 1H, —CH—), 3.72 (d, J=10.8 Hz, 3H, —OCH$_3$), 3.54 (d, J=10.5 Hz, 3H, —OCH$_3$), 3.30-3.19 (m, 4H, 2*—CH$_2$), 3.00-2.90 (m, 2H, —CH$_2$), 2.72 (d, J=10.8 Hz, 3H, —CH$_3$). MS (ES+) m/z 453 [M-(HCl)+H]$^+$.

1-(2'-Acetylaminobiphenyl-4-ylmethyl)-6,7-dimethoxy-3,4-dihydro-1H-isoquinoline-2-carboxylic acid tert-butyl ester (17)

Ethylacetate-hexane (20:80 to 60:40 v/v) was used as eluent for flash column chromatography (67%). MS (ES+) m/z 539 (M+Na)$^+$.

N-[4'-(6,7-Dimethoxy-1,2,3,4-tetrahydroisoquinolin-1-ylmethyl)biphenyl-2-yl]acetamide hydrochloride salt (18)

The product was obtained in 66% yield as white powder. $^1$H NMR (300 MHz, DMSO-d$_6$) δ 9.47-9.31 (bs, 1H, —NH), 9.23 (s, 2H, —NH$_2$), 7.50-7.30 (m, 8H, ArH), 6.80 (s, 1H, ArH), 6.57 (s, H, ArH), 4.71 (s, 1H, —CH—), 3.74 (s, 3H, —OCH$_3$), 3.57 (s, 3H, —OCH$_3$), 3.41-3.36 (m, 2H, —CH$_2$), 3.29-3.17 (m, 2H, —CH$_2$), 3.03-2.88 (m, 2H, —CH$_2$), 1.84 (s, 3H, —CH$_3$). MS (ES+) m/z 417 [M-(HCl)+H]$^+$.

6,7-Dimethoxy-1-[4-(4-methoxypyridin-3-yl)benzyl]-3,4-dihydro-1H-isoquinoline-2-carboxylic acid tert-butyl ester (20); 6,7-Dimethoxy-1-[4-(4-methoxypyridin-3-yl)benzyl]-1,2,3,4-tetrahydroisoquinolinehydrochloride (21)

The product was obtained as pale yellow powder with 86% yield. $^1$H NMR (300 MHz, DMSO-d$_6$) δ 9.63 (s, 2H, —NH$_2$), 8.84-8.82 (m, 1H, ArH), 8.71 (s, 1H, ArH), 7.74-7.72 (m, 1H, ArH), 7.63-7.60 (m, 2H, ArH), 7.52-7.50 (m, 2H, ArH), 6.80 (s, H, ArH), 6.38 (s, H, ArH), 4.72 (s, 1H, —CH—), 4.12 (s, 3H, —OCH$_3$), 3.73 (s, 3H, —OCH$_3$), 3.49 (s, 3H, —OCH$_3$), 3.44-3.38 (m, 4H, 2*—CH$_2$), 3.00-2.95 (m, 2H, —CH$_2$). MS (ES+) m/z 391 [M-(HCl)+H]$^+$.

6,7-Dimethoxy-1-[4-(4-methoxypyridin-3-yl)benzyl]-2-methyl-1,2,3,4-tetrahydroisoquinoline hydrochloride (23)

The product was obtained as yellow powder. $^1$H NMR (300 MHz, DMSO-d$_6$) δ 11.30 (s, 1H, —NH), 8.83 (s, 1H, ArH), 8.71 (s, 1H, ArH), 7.71 (s, 1H, ArH), 7.62-7.51 (m, 2H, ArH), 7.41-7.29 (m, 2H, ArH), 6.84 (s, 1H, ArH), 5.72 (s, 1H, ArH), 4.66 (s, 1H, —CH—), 4.07 (s, 3H, —OCH$_3$), 3.72 (s, 6H, 2*—OCH$_3$), 3.26 (s, 3H, —NCH$_3$), 3.13-2.92 (m, 4H, 2*—CH$_2$), 2.88-2.76 (m, 2H, —CH$_2$). MS (ES+) m/z 406 [M-(HCl)+H]$^+$.

1-[4-(2,4-Dimethoxypyrimidin-5-yl)benzyl]-6,7-dimethoxy-3,4-dihydro-1H-isoquinoline-2-carboxylic acid tert-butyl ester (25); 1-[4-(2,4-Dimethoxypyrimidin-5-yl)benzyl]-6,7-dimethoxy-1,2,3,4-tetrahydroisoquinoline hydrochloride (26)

The product was obtained in 80% yield as pale yellow powder. $^1$H NMR (300 MHz, DMSO-d$_6$) δ 11.25 (s, 1H, —NH), 11.19 (s, 1H, —NH), 9.38 (s, 2H, —NH$_2$), 8.37 (s, 1H, ArH), 7.62-7.53 (m, 2H, ArH), 7.44-7.32 (m, 2H, ArH), 6.80 (s, 1H, ArH), 6.43 (d, J=3.6 Hz, 1H, ArH), 4.69 (s, 1H, —CH—), 4.13 (s, 3H, —OCH$_3$), 3.95 (s, 3H, —OCH$_3$), 3.73 (s, 3H, —OCH$_3$), 3.51 (s, 3H, —OCH$_3$), 3.45-3.26 (m, 4H, 2*—CH$_2$), 3.06-2.95 (m, 2H, —CH$_2$). MS (ES+) m/z 422 [M-(2HCl)+H]$^+$.

6,7-Dimethoxy-1-(4-pyrimidin-5-ylbenzyl)-3,4-dihydro-1H-isoquinoline-2-carboxylic acid tert-butyl ester (28); 6,7-Dimethoxy-1-(4-pyrimidin-5-ylbenzyl)-1,2,3,4-tetrahydroisoquinoline hydrochloride (29)

The product was obtained in 86% yield as pale yellow powder. $^1$H NMR (300 MHz, DMSO-d$_6$) δ 9.36 (s, 2H, —NH$_2$), 9.26-9.15 (m, 3H, ArH), 7.85 (d, J=7.5 Hz, 2H, ArH), 7.55 (d, J=7.8 Hz, 2H, ArH), 6.80 (s, 1H, ArH), 6.55 (s, 1H, ArH), 4.72 (s, 1H, —CH—), 3.73 (s, 3H, —OCH$_3$), 3.54 (s, 3H, —OCH$_3$), 3.42-3.27 (m, 4H, 2*—CH$_2$), 3.05-2.94 (m, 2H, —CH$_2$). MS (ES+) m/z 362 [M-(2HCl)+H]$^+$.

1-[4-(2-Chloro-pyridin-3-yl)benzyl]-6,7-dimethoxy-3,4-dihydro-1H-isoquinoline-2-carboxylic acid tert-butyl ester (31); 1-[4-(2-Chloro-pyridin-3-yl)benzyl]-6,7-dimethoxy-1,2,3,4-tetrahydroisoquinoline hydrochloride (32)

The product was obtained in 94% yield as pale yellow powder. $^1$H NMR (300 MHz, DMSO-d$_6$) δ 9.45 (s, 2H, —NH$_2$), 8.46-8.44 (m, 1H, ArH), 7.87-7.85 (m, 1H, ArH), 7.57-7.47 (m, 5H, ArH), 6.81 (s, 1H, ArH), 6.39 (s, 1H, ArH), 4.75 (s, 1H, —CH—), 3.74 (s, 3H, —OCH₃), 3.50 (s, 3H, —OCH₃), 3.43-3.29 (m, 4H, 2*—CH₂), 3.06-2.90 (m, 2H, —CH₂). MS (ES+) m/z 395 [M-(2HCl)+H]⁺.
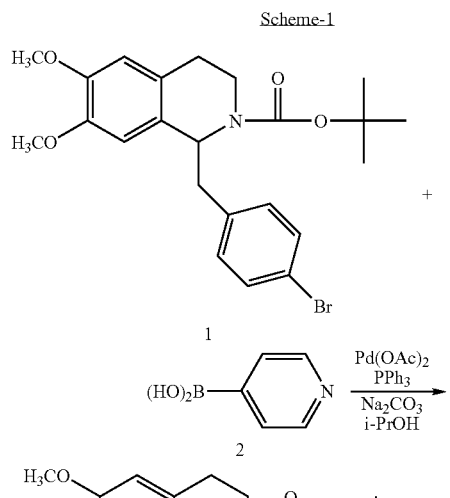
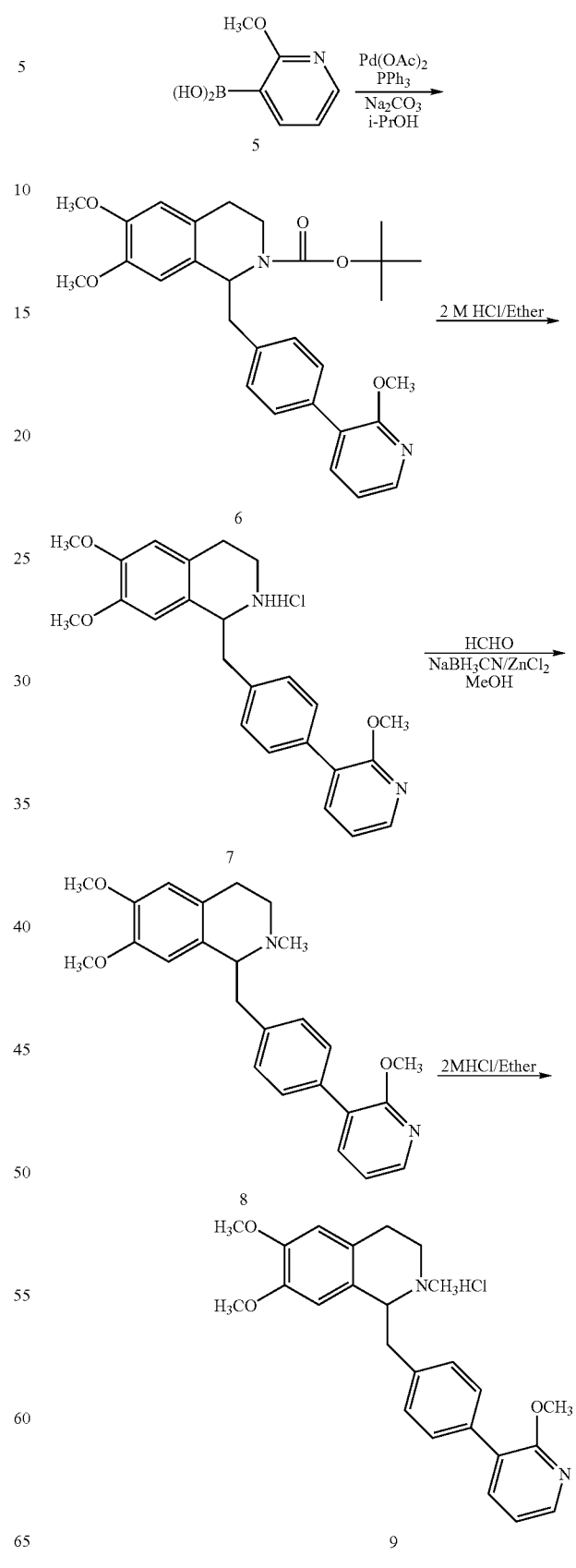
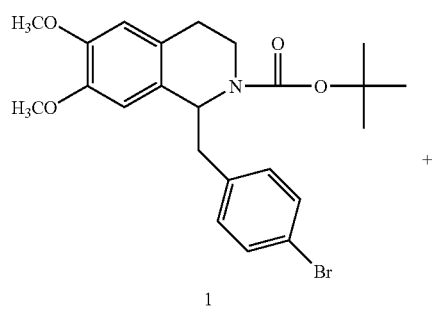

Scheme-3
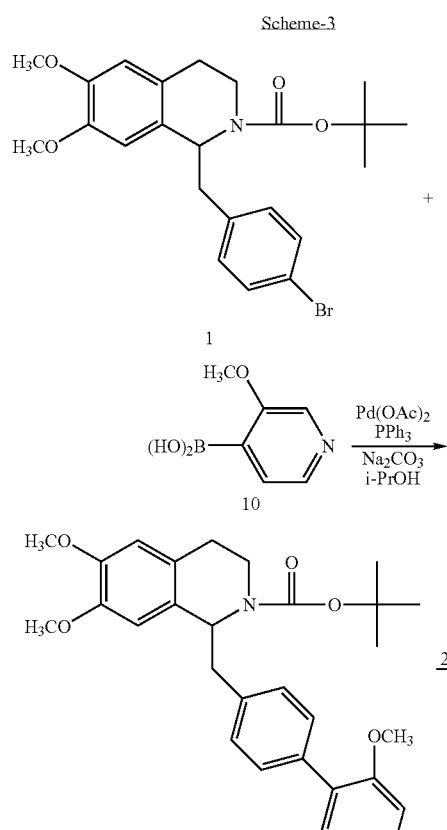
Scheme-4
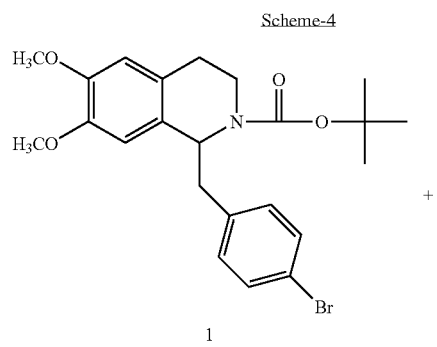
Scheme-5
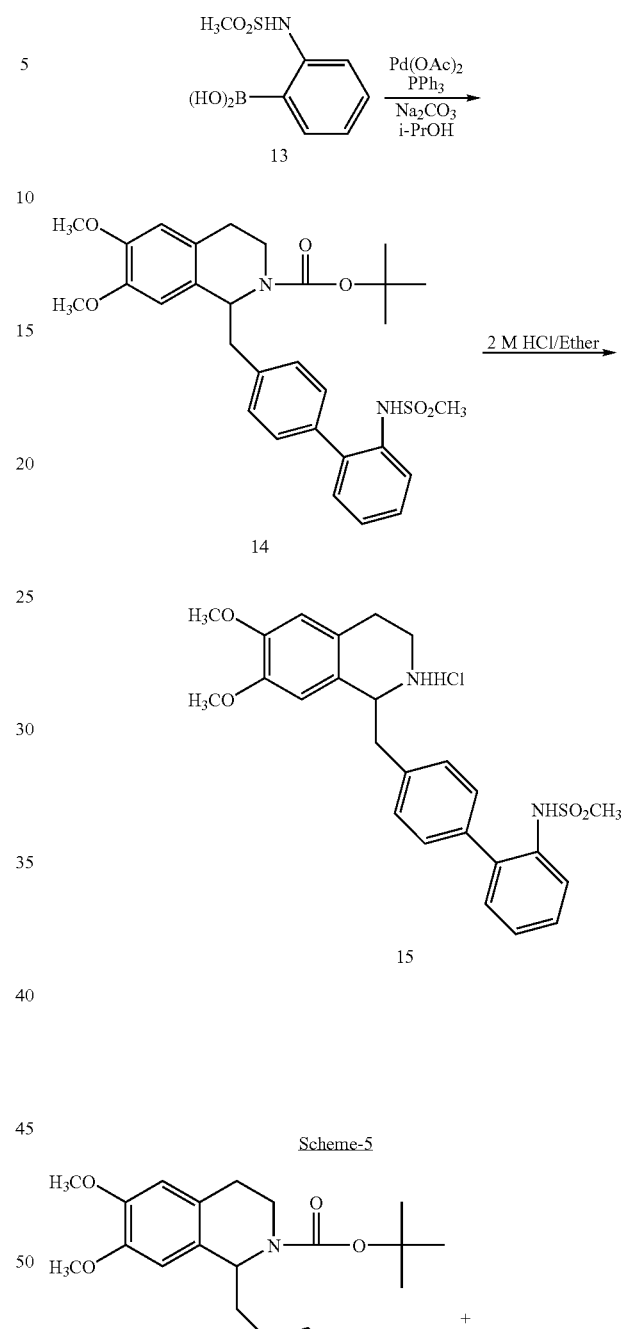
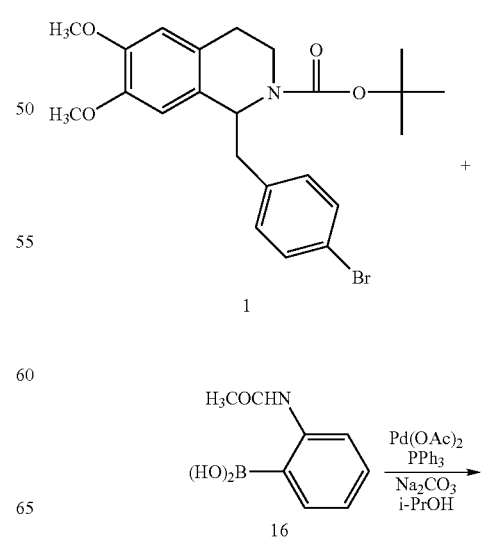

19
-continued
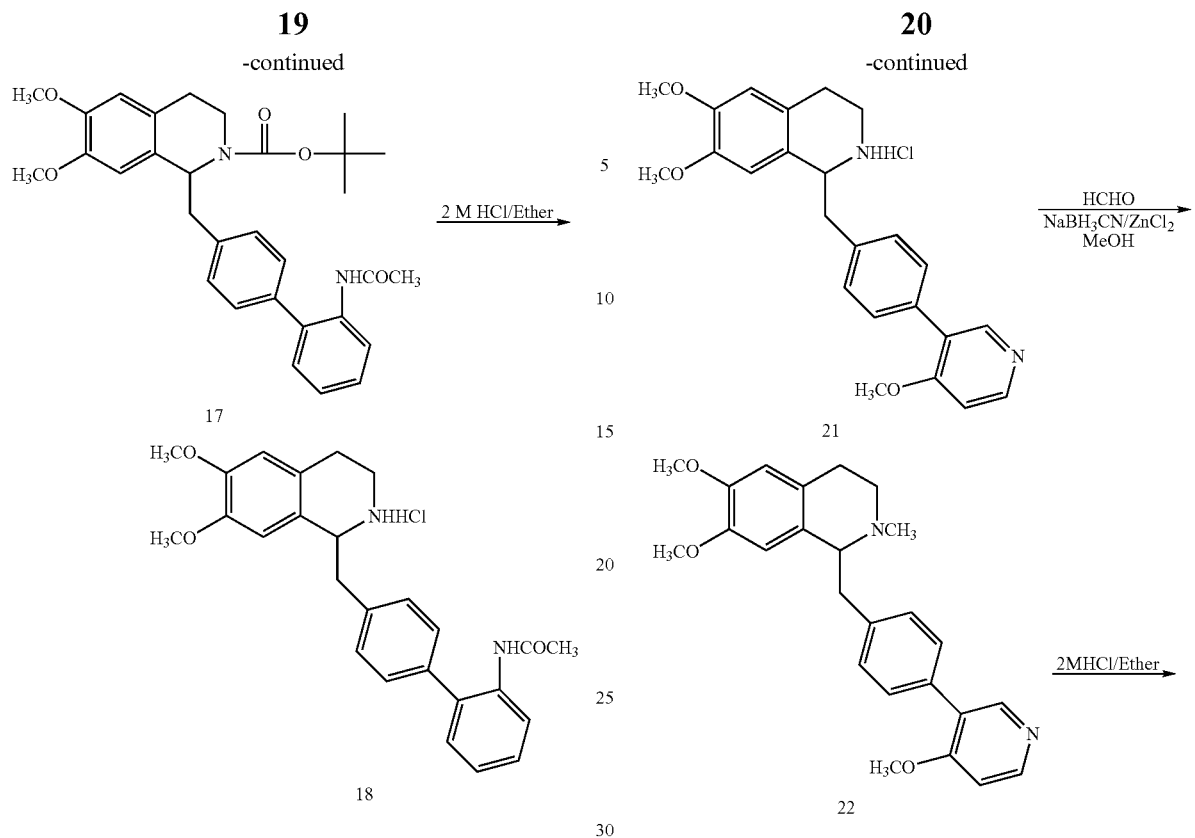
20
-continued
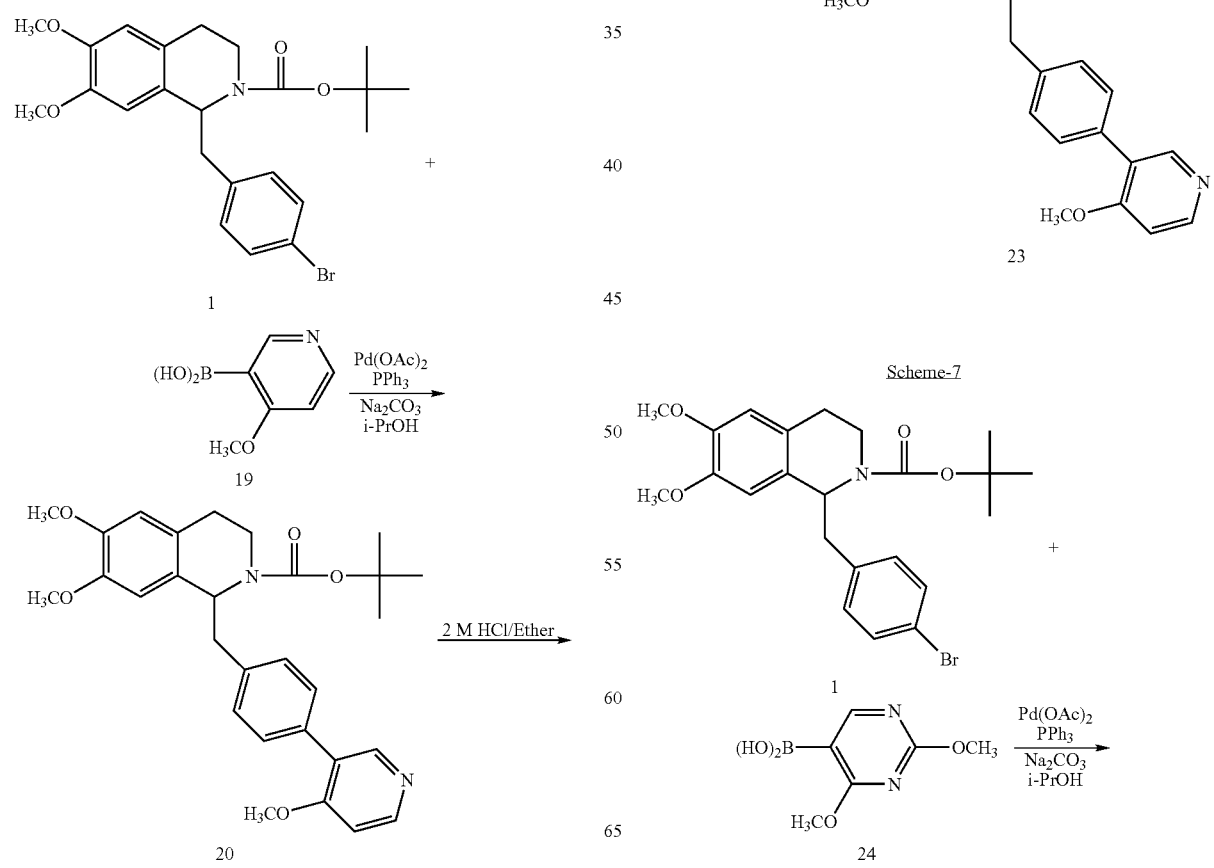

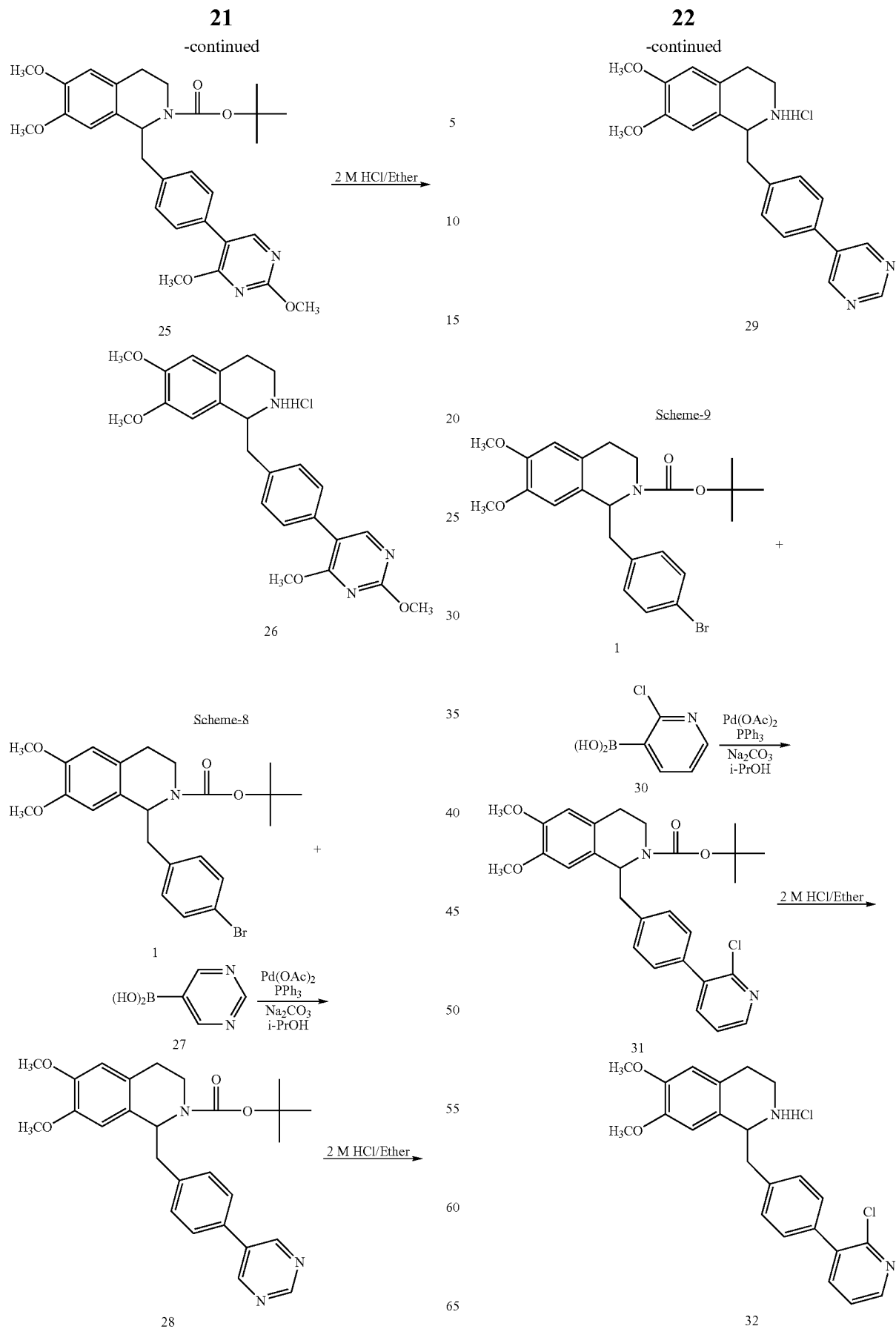

TABLE I

| STRUCTURE | Molecular Formula | Molecular Weight | Log P | EC50 μM Astrocyte | EC50 μM C6 |
|---|---|---|---|---|---|
| 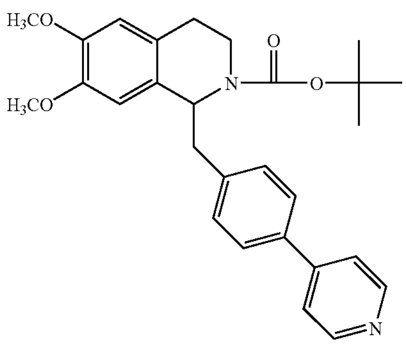 [SMILES: COc1cc2c(cc1OC)C(Cc1ccc(-c3ccncc3)cc1)N(C(=O)OC(C)(C)C)CC2] | $C_{28}H_{32}N_2O_4$ | 460.56 | 4.76 | 18.38 | 5.915 |
| 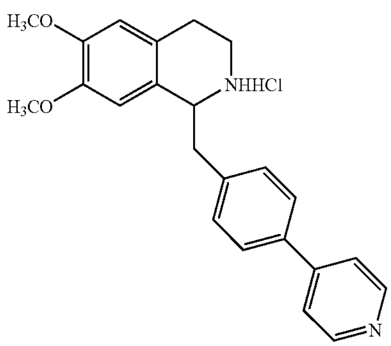 | $C_{24}H_{29}ClN_2O_2$ | 412.95 | 3.66 | 74.43 | 17.68 |
| 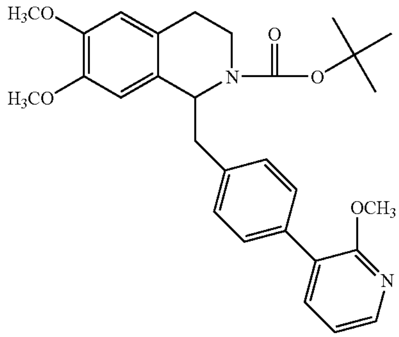 [SMILES: COc1cc2c(cc1OC)C(Cc1ccc(-c3cccnc3OC)cc1)N(C(=O)OC(C)(C)C)CC2] | $C_{29}H_{34}N_2O_5$ | 490.59 | 5.35 | No Effect | 4.3 |
| 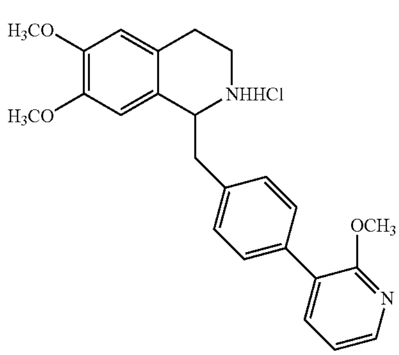 | $C_{24}H_{27}ClN_2O_3$ | 426.94 | 4.24 | 50-100 | 1.75 |

TABLE I-continued

| STRUCTURE | Molecular Formula | Molecular Weight | Log P | EC50 μM Astrocyte | EC50 μM C6 |
|---|---|---|---|---|---|
| 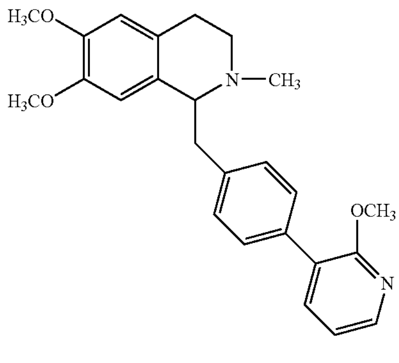 [SMILES: COc1cc2c(cc1OC)C(Cc1ccc(-c3cccnc3OC)cc1)N(C)CC2] | $C_{25}H_{28}N_2O_3$ | 404.50 | 4.62 | 27.3 | 2.2 |
| | $C_{25}H_{29}Cl_1N_2O_3$ | 440.96 | 4.62 | 25.3 | 5.5 |
| 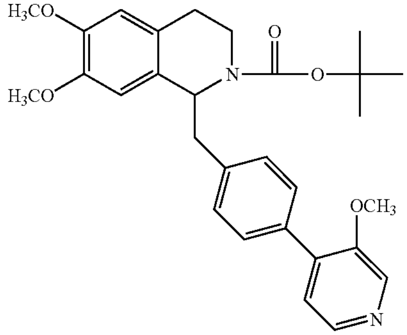 [SMILES: COc1cc2c(cc1OC)C(Cc1ccc(-c3ccncc3OC)cc1)N(C(=O)OC(C)(C)C)CC2] | $C_{29}H_{34}N_2O_5$ | 490.59 | 4.64 | 13.6 | 4.4 |
| 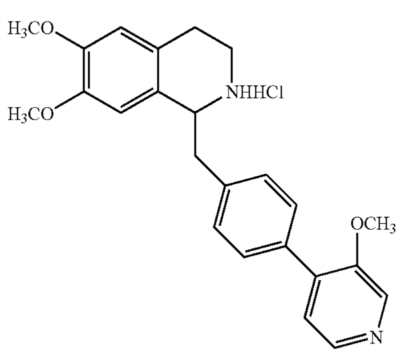 | $C_{24}H_{27}ClN_2O_3$ | 426.94 | 3.53 | 49.5 | 6.9 |

TABLE I-continued

| STRUCTURE | Molecular Formula | Molecular Weight | Log P | EC50 μM Astrocyte | EC50 μM C6 |
|---|---|---|---|---|---|
| 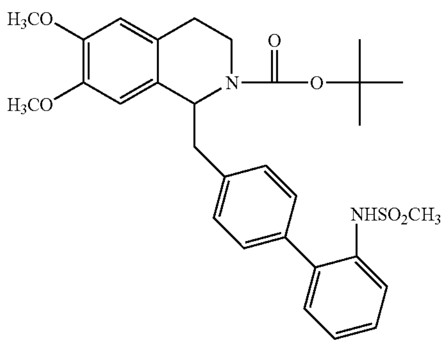 | $C_{30}H_{36}N_2O_6S$ | 552.68 | 4.32 | No Effect | 6.2 |
| 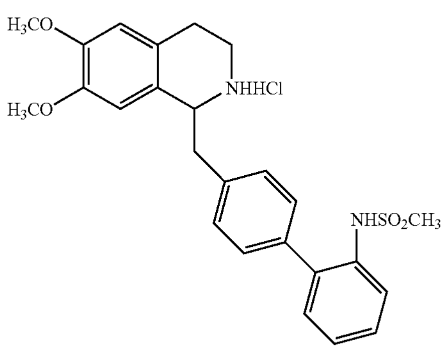 | $C_{25}H_{29}ClN_2O_4S$ | 489.03 | 3.21 | 50-100 | 8.9 |
| 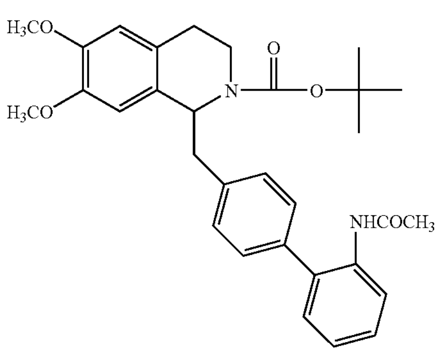 | $C_{31}H_{36}N_2O_5$ | 516.63 | 5.01 | No Effect | 9.2 |
| 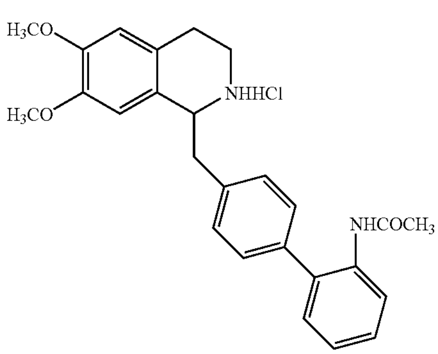 | $C_{26}H_{29}ClN_2O_3$ | 452.97 | 3.90 | No Effect | 22.4 |

TABLE I-continued

| STRUCTURE | Molecular Formula | Molecular Weight | Log P | EC50 μM Astrocyte | EC50 μM C6 |
|---|---|---|---|---|---|
| 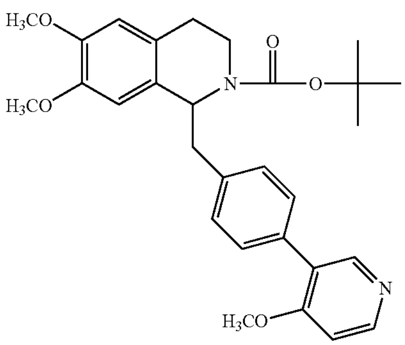 [SMILES: COc1cc2c(cc1OC)C(Cc1ccc(-c3cnccc3OC)cc1)N(C(=O)OC(C)(C)C)CC2] | $C_{29}H_{34}N_2O_5$ | 490.59 | 4.64 | 12.2 | 5.9 |
| 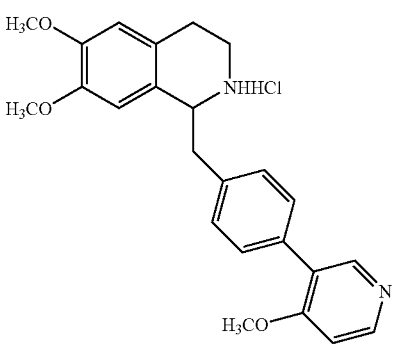 | $C_{24}H_{27}ClN_2O_3$ | 426.94 | 3.53 | 22.8 | 0.6 |
| 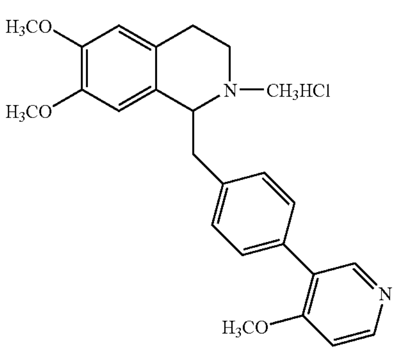 | $C_{25}H_{29}ClN_2O_3$ | 440.96 | 3.91 | 28.2 | 3.3 |
| 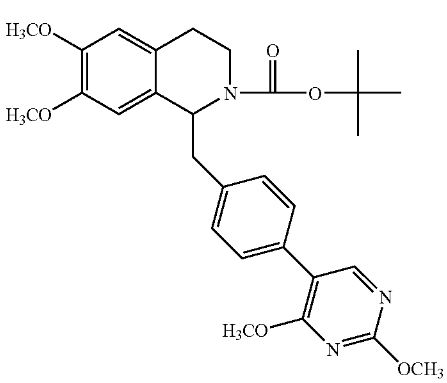 [SMILES: COc1ncc(-c2ccc(CC3c4cc(OC)c(OC)cc4CCN3C(=O)OC(C)(C)C)cc2)c(OC)n1] | $C_{29}H_{35}N_3O_6$ | 521.60 | 5.14 | No Effect | 6.8 |

TABLE I-continued

| STRUCTURE | Molecular Formula | Molecular Weight | Log P | EC50 μM Astrocyte | EC50 μM C6 |
|---|---|---|---|---|---|
| 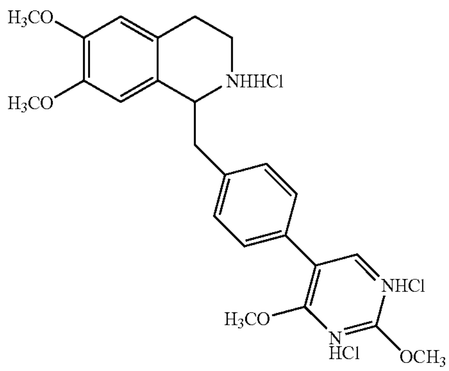 | $C_{24}H_{30}Cl_3N_3O_4$ | 530.87 | 4.03 | 34.0 | 9.3 |
| 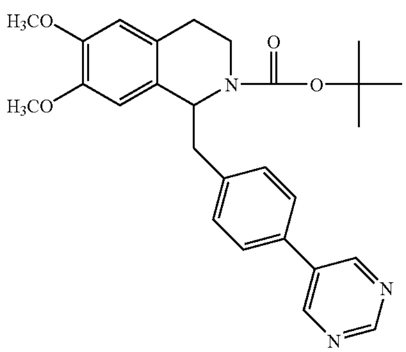 [SMILES: COc1cc2c(cc1OC)C(Cc1ccc(-c3cncnc3)cc1)N(C(=O)OC(C)(C)C)CC2] | $C_{27}H_{31}N_3O_4$ | 461.55 | 4.17 | No Effect | 15.2 |
| 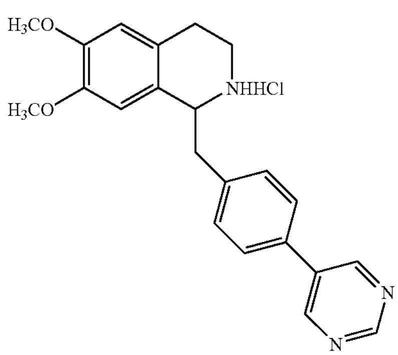 | $C_{22}H_{24}ClN_3O_2$ | 397.90 | 3.06 | No Effect | 39.4 |
| 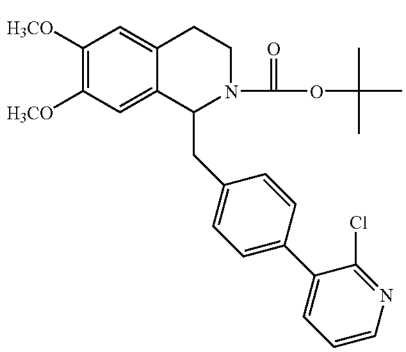 [SMILES: COc1cc2c(cc1OC)C(Cc1ccc(-c3cccnc3Cl)cc1)N(C(=O)OC(C)(C)C)CC2] | $C_{28}H_{31}ClN_2O_4$ | 495.01 | 5.66 | No Effect | 3.5 |

TABLE I-continued

| STRUCTURE | Molecular Formula | Molecular Weight | Log P | EC50 μM Astrocyte | EC50 μM C6 |
|---|---|---|---|---|---|
| [structure: 6,7-dimethoxy-tetrahydroisoquinoline with NHHCl, CH2-phenyl-(2-chloropyridin-3-yl)] | $C_{23}H_{24}Cl_2N_2O_2$ | 431.35 | 4.56 | 28.2 | 2.7 |

The synthesis of N-(2-Benzo[1,3]dioxol-5-yl-ethyl)-2-(4-bromophenyl)acetamide 35, 5-(4-bromobenzyl)-5,6,7,8-tetrahydro-[1,3]dioxolo[4,5-g]isoquinoline oxalate salt 37, and 5-(4-Bromobenzyl)-7,8-dihydro-5H-[1,3]dioxolo[4,5-g]isoquinoline-6-carboxylic acid tert-butyl ester 38 is shown in scheme-10. Compound 35 was synthesized by coupling of 2-Benzo[1,3]dioxol-5-yl-ethylamine hydrochloride salt 33 with 4-bromophenyl acetic acid 34 using diethyl cyanophosphonate in the presence of triethyl amine in DMF. The amide 35 was cyclized by Bischler Napieralski reaction using POCl3 in anhydrous acetonitrile to get 5-(4-bromobenzyl)-7,8-dihydro-[1,3]dioxolo[4,5-g]isoquinoline 36 which was reduced by NaBH4 and converted to an oxalate salt 37 using oxalic acid dihydrate in methanol. The compound 37 was treated with 1N NaOH in dichloromethane to obtain free amine and this amine was protected with di-tert-butyl dicarbonate in the presence of 1N NaOH in THF to afford compound 38.

5-[4-(4-Chloropyridin-3-yl)benzyl]-7,8-dihydro-5H-[1,3]dioxolo[4,5-g]isoquinoline-6-carboxylic acid tert-butyl ester 40 was synthesized by the Suzuki coupling of compound 38 with 4-chloro pyridine-3-boronic acid pinacol ester 39 using Palladium(II) acetate, triphenylphosphine, and $Na_2CO_3$ in anhydrous DMF. Compound 40 was treated with trifluoro acetic acid in dichloromethane to get compound 5-[4-(4-chloropyridin-3-yl)-benzyl]-5,6,7,8-tetrahydro-[1,3]dioxolo[4,5-g]isoquinoline trifluoroacetate 41. 5-[4-(4-chloropyridin-3-yl)benzyl]-5,6,7,8-tetrahydro-[1,3]dioxolo[4,5-g]isoquinoline dihydrochloride salt 42 was accomplished by treating compound 41 using 37% HCl, 1N NaOH followed by 2M HCl/Ether in MeOH-Ether (Scheme-11).

The synthesis of 5-[4-(4-methoxypyridin-3-yl)benzyl]-5,6,7,8-tetrahydro-[1,3]dioxolo[4,5-g]isoquinoline dihydrochloride salt 45 is shown in Scheme-12. Reaction of compound 38 with 4-methoxypyridine-3-boronic acid 19 in the presence of Palladium (II) acetate, triphenylphosphine, and $Na_2CO_3$ in anhydrous 2-propanol yielded 5-[4-(4-methoxypyridin-3-yl)benzyl]-7,8-dihydro-5H-[1,3]dioxolo[4,5-g]isoquinoline-6-carboxylic acid tert-butyl ester 43 which was treated with trifluoroacetic acid in dichloromethane to get 5-[4-(4-methoxypyridin-3-yl)benzyl]-5,6,7,8-tetrahydro-[1,3]dioxolo[4,5-g]isoquinoline trifluoro acetate salt 44. Compound 44 was treated by 37% HCl, 1N NaOH followed by 2M HCl/Ether in MeOH-Ether to obtain 45.

N-(2-Benzo[1,3]dioxol-5-yl-ethyl)-2-(4-bromophenyl)acetamide 35

To a stirred solution of 4-bromophenyl acetic acid 34 (2.000 g, 9.300 mmol) and 2-benzo[1,3]dioxol-5-yl-ethylamine hydrochloride salt 33 (2.063 g, 10.230 mmol) in anhydrous DMF (25 mL) was added triethyl amine (2.823 g, 27.900 mmol) followed by diethyl cyanophosphonate (1.669 g, 10.230 mmol) at $^0$0 C and the reaction mixture was stirred at room temperature overnight, poured into ice-water. The precipitated was filtered, washed with water and air-dried. The crude product was recrystallized using $CHCl_3$-Hexane to get compound 35 as a white sold (3.133 g, 93%). $^1$H NMR (300 MHz, DMSO-$d_6$) δ 8.06 (t, J=5.1 Hz, 1H, —NH), 7.47 (d, J=8.4 Hz, 2H, ArH), 7.16 (d, J=8.1 Hz, 2H, ArH), 6.79 (d, J=7.8 Hz, 1H, ArH), 6.74 (s, 1H, ArH), 6.60 (d, J=7.8 Hz, 1H, ArH), 5.96 (s, 2H, —$CH_2$), 3.35 (s, 2H, —$CH_2$), 3.32 (q, J=6.9 Hz, 2H, —$CH_2$), 2.60 (t, J=7.2 Hz, 2H, —$CH_2$). MS (ES+) m/z 384 (M+Na)$^+$.

5-(4-Bromobenzyl)-5,6,7,8-tetrahydro-[1,3]dioxolo[4,5-g]isoquinoline oxalate salt 37

Phosphorus oxychloride (119.372 g, 778.83 mmol) was added to a stirred solution of N-(2-benzo[1,3]dioxol-5-yl-ethyl)-2-(4-bromophenyl)acetamide 35 (9.400 g, 25.951 mmol) in anhydrous acetonitrile (225 mL) and refluxed for 6 h. The reaction mixture was concentrated under reduced pressure, methanol was added to it, and again concentrated the solvent under reduced pressure. The obtained residue was dissolved in methanol, to this solution was added sodium borohydride (17.700 g, 467.118 mmol) and the mixture was stirred overnight at room temperature. The solvent was removed under reduced pressure, the residue was dissolved in $CHCl_3$, washed with 1N NaOH solution, water and dried over $Na_2SO_4$. The organic layer was evaporated under reduced pressure and the oily mass was dissolved in $CHCl_3$. A solution of oxalicacid dihydrate (6.543 g, 51.902 mmol) in methanol was added to above solution with stirring at room temperature followed by addition of ether. The mixture was stirred for 2 h at the same temperature and kept in the refrigerator overnight. Filtered the solid and washed with ether, and air dried to afford 37 as white solid (9.5 g, 84%). $^1$H NMR (300 MHz, DMSO-$d_6$) δ 7.55 (d, J=7.5 Hz, 2H, ArH), 7.31 (d, J=7.8 Hz, 2H, ArH), 6.79 (s, 1H, ArH), 6.73 (s, 1H, ArH), 5.99 (s, 2H, $CH_2$), 4.63 (t, J=6.3 Hz, 1H, —CH), 3.36-3.32 (m, 2H, $CH_2$), 3.18-3.06 (m, 2H, $CH_2$), 2.96-2.82 (m, 2H, —$CH_2$). MS (ES+) m/z 346 [M-$(COOH)_2$+H]$^+$.

5-(4-Bromobenzyl)-7,8-dihydro-5H-[1,3]dioxolo[4,5-g]isoquinoline-6-carboxylic acid tert-butyl ester 38

To a solution of 5-(4-bromobenzyl)-5,6,7,8-tetrahydro-[1,3]dioxolo[4,5-g]isoquinoline oxalate salt 37 (9.400 g, 21.547 mmol) in dichloromethane (300 mL) was added 1N NaOH (430 mL), and the mixture was stirred at room temperature for 2 h. Separated the two layers, the aqueous layer was extracted with dichloromethane (2×100 mL) and dried over $Na_2SO_4$. The solvents were removed under reduced pressure to obtain free amine as yellow oil which was dissolved in tetrahydro furan (100 mL). To this solution was added 1N NaOH aqueous solution (85 mL) followed by di-t-butyl dicarbonate (7.054 g, 32.320 mmol) in tetrahydro furan (70 mL) at 0° C. The reaction mixture was stirred overnight at room temperature, and the solvents were concentrated under reduced pressure. The residue was diluted with water, and extracted with dichloromethane. The organic layer was dried over $Na_2SO_4$, and evaporated under reduced pressure. Crude residue was purified by flash column chromatography using EtOAc-Hexanes (30:70 to 40:60 v/v) to give white solid powder 38 (7.405 g, 77%). In the NMR spectrum, two sets of peaks were appeared in the ratio of 1:2. $^1$H NMR (300 MHz, DMSO-d6) δ 7.49-7.41 (m, 3H, ArH), 7.22-7.11 (m, 3H, ArH), 7.00 (s, 1H, ArH), 6.85 (s, 1H, ArH), 6.89 (s, 1H, ArH), 5.14 (s, 1H, —CH—), 5.04-5.00 (m, 1H, —CH—), 3.31-3.16 (m, 2H, —$CH_2$), 3.03-2.84 (m, 3H, —$CH_2$), 2.70-2.49 (m, 3H, —$CH_2$). MS (ES+) m/z 468 (M+Na)$^+$.

5-[4-(4-Chloropyridin-3-yl)benzyl]-7,8-dihydro-5H-[1,3]dioxolo[4,5-g]isoquinoline-6-carboxylic acid tert-butyl ester 40

A mixture of 4-chloro pyridine-3-boronic acid pinacol ester 39 (0.515 g, 2.150 mmol), 5-(4-bromobenzyl)-7,8-dihydro-5H-[1,3]dioxolo[4,5-g]isoquinoline-6-carboxylic acid tert-butyl ester 38 (0.800 g, 1.792 mmol), Palladium(II) acetate (0.016 g, 0.072 mmol), triphenylphosphine (0.038 g, 0.143 mmol) and $Na_2CO_3$ (0.760 g, 7.169 mmol) in anhydrous DMF (20 mL) was refluxed for 16 h. The reaction mixture was cooled to room temperature, filtered through silica, washed with ethyl acetate. The solvents were extracted with water, dried over $Na_2SO_4$ and evaporated under reduced pressure. The crude product was purified by flash column chromatography using EtOAc-Hexanes (20:80 to 40:60 v/v) to get light yellow oily mass 38 (0.250 g, 29%). MS (ES+) m/z 501 (M+Na)$^+$.

5-[4-(4-Chloropyridin-3-yl)benzyl]-5,6,7,8-tetrahydro-[1,3]dioxolo[4,5-g]isoquinoline dihydrochloride salt 42

To a solution of 5-[4-(4-chloropyridin-3-yl)benzyl]-7,8-dihydro-5H-[1,3]dioxolo[4,5-g]isoquinoline-6-carboxylic acid tert-butyl ester 40 (0.220 g, 0.459 mmol) in anhydrous dichloromethane (10 mL) was added trifluoroacetic acid (4.190 g, 36.744 mmol) at 0° C., the reaction mixture was warmed to room temperature and stirred at the same temperature for 2 h. The mixture was concentrated under reduced pressure, repeatedly evaporated using dichloromethane. The residue was treated with aqueous HCl and filtered. The filtrates were basified using 1N NaOH, extracted with $CHCl_3$, washed with water, dried over $Na_2SO_4$ and evaporated under reduced pressure. The oily mass was dissolved in MeOH (15 mL) and then in diethyl ether (60 mL). 2 M HCl solution in diethylether (30 mL) was added to above solution at 0° C., the mixture was warmed to room temperature and stirred overnight. Filtered the reaction mixture, the residue was washed with ether, crystallized from methanol-ether to afford 42 as off white-solid (0.103 g, 50%). $^1$H NMR (300 MHz, DMSO-d$_6$) δ 9.33 (bs, 2H, —$NH_2$), 8.62 (s, 1H, ArH), 8.59 (d, J=5.4 Hz, 1H, ArH), 7.76 (d, J=5.4 Hz, 1H, ArH), 7.55 (s, 4H, ArH), 6.83 (s, 1H, ArH), 6.79 (s, 1H, ArH), 6.00 (s, 2H, —$CH_2$), 4.72 (s, 1H, —CH—), 3.48-3.17 (m, 4H, 2*—$CH_2$), 3.08-2.86 (m, 2H, —$CH_2$). MS (ES+) m/z 379 [M-(2HCl)+H]$^+$.

5-[4-(4-methoxypyridin-3-yl)benzyl]-7,8-dihydro-5H-[1,3]dioxolo[4,5-g]isoquinoline-6-carboxylic acid tert-butyl ester 43

A mixture of 4-methoxy pyridine-3-boronic acid hydrate 19 (0.716 g, 4.684 mmol), 5-(4-bromobenzyl)-7,8-dihydro-5H-[1,3]dioxolo[4,5-g]isoquinoline-6-carboxylic acid tert-butyl ester 38 (1.043 g, 2.342 mmol), Palladium(II) acetate (0.021 g, 0.094 mmol), triphenylphosphine (0.049 g, 0.187 mmol) and $Na_2CO_3$ (0.993 g, 9.368 mmol) in anhydrous 2-propanol (20 mL) was refluxed for 16 h. The reaction mixture was cooled to room temperature, filtered through silica, washed with ethyl acetate. The solvents were concentrated under reduced pressure. The crude residue was purified by flash column chromatography using Acetone-Hexanes (20:80 to 50:60 v/v) to yield 43 (0.389 g, 35%). MS (ES+) m/z 497 (M+Na)$^+$.

5-[4-(4-methoxypyridin-3-yl)benzyl]-5,6,7,8-tetrahydro-[1,3]dioxolo[4,5-g]isoquinoline dihydrochloride salt 45

Compound 45 was synthesized according to procedure of 42. The product was obtained in 80% yield as off-white powder. $^1$H NMR (300 MHz, DMSO-d$_6$) δ 9.56 (bs, 2H, —$NH_2$), 8.84-8.72 (m, 2H, ArH), 7.72 (d, J=6.9 Hz, 1H, ArH), 7.64-7.54 (m, 4H, ArH), 6.82 (s, 1H, ArH), 6.78 (s, 1H, ArH), 6.00 (s, 2H, —$CH_2$), 4.71 (s, 1H, —CH—), 3.20-2.85 (m, 6H, 3*—$CH_2$). MS (ES+) m/z 375 [M-(2HCl)+H]$^+$.

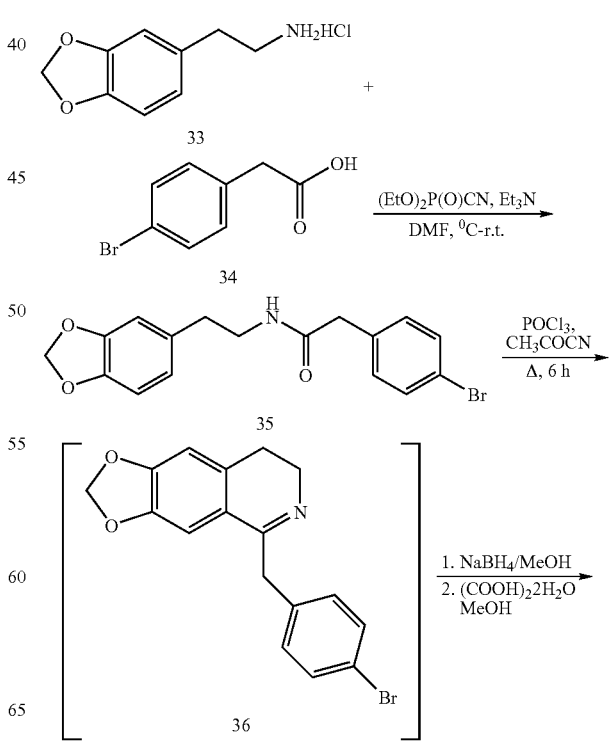

Scheme-10

37
38
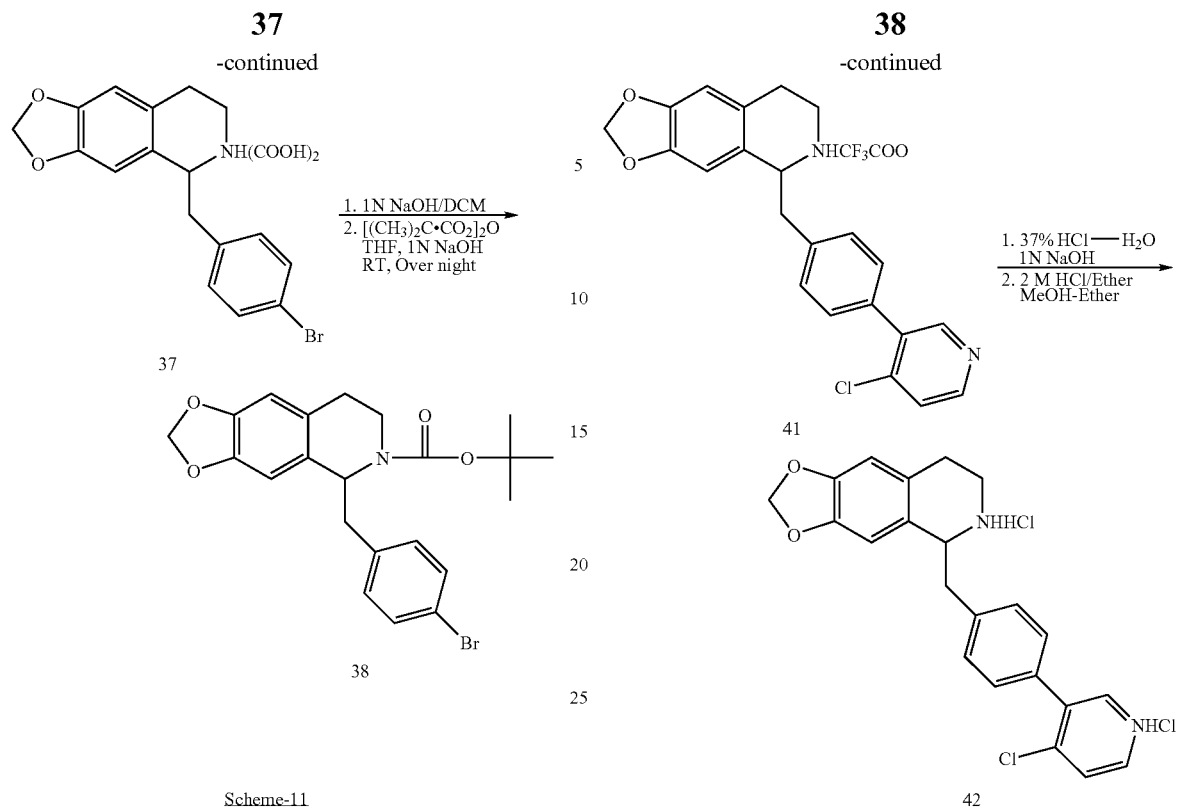
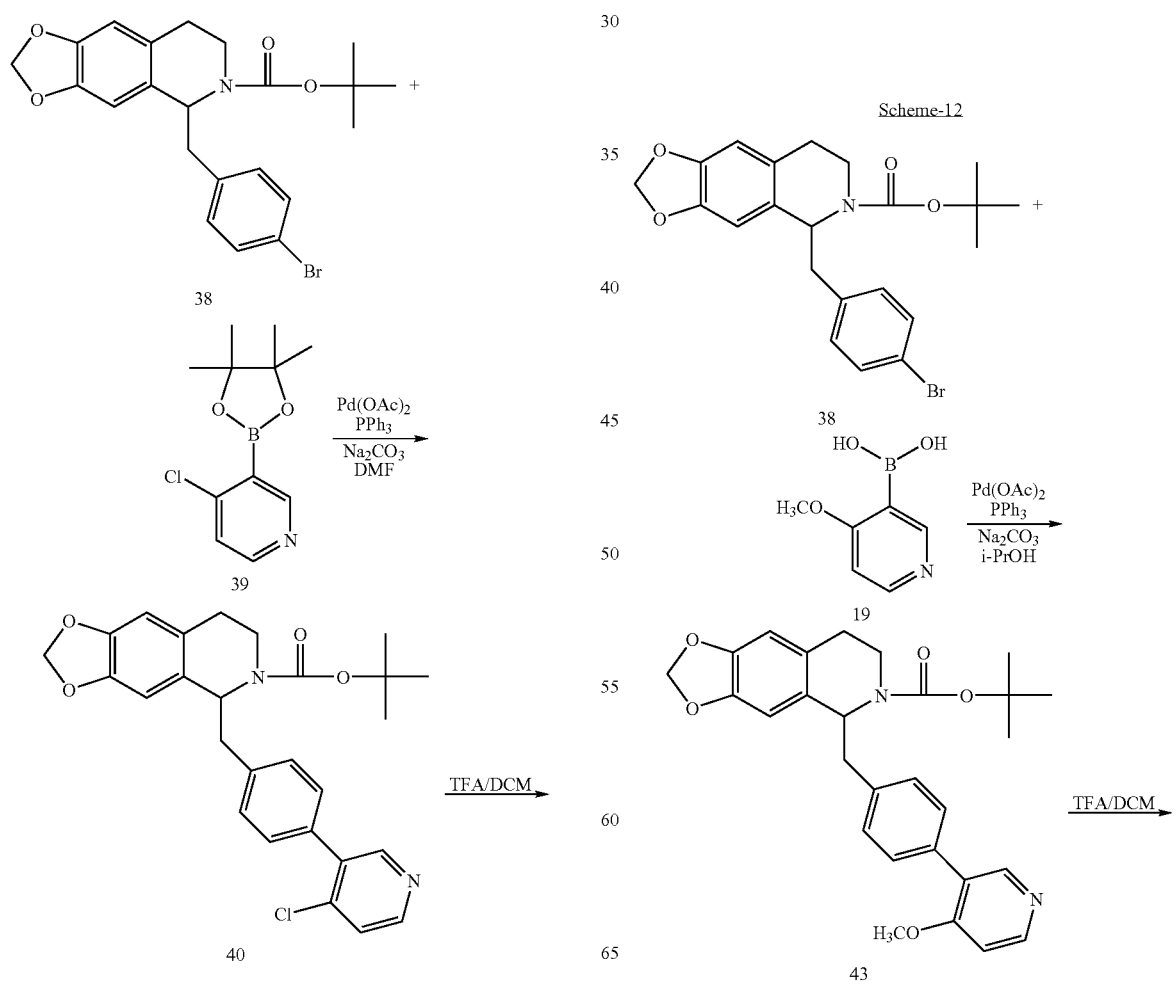

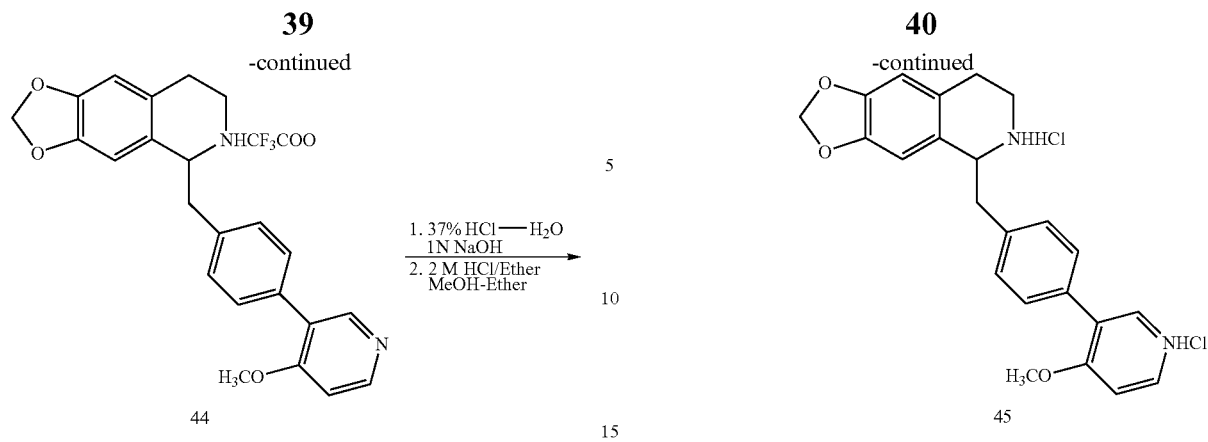
TABLE 2
| STRUCTURE | Molecular Formula | Molecular Weight | Log P | EC50 μM Astrocyte | EC50 μM C6 |
|---|---|---|---|---|---|
| 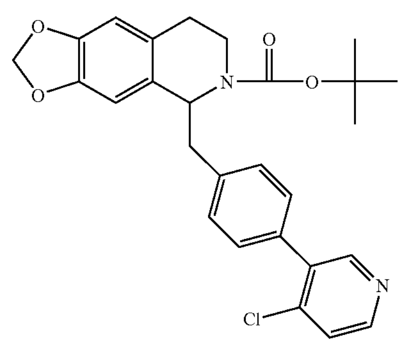 [SMILES: CC(C)(C)OC(=O)N1CCc2cc3c(cc2C1Cc1ccc(-c2cnccc2Cl)cc1)OCO3] | $C_{27}H_{27}ClN_2O_4$ | 478.97 | 5.35 | 37.5 | 6.3 |
| 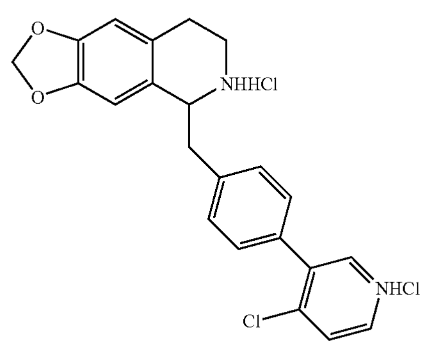 | $C_{22}H_{21}Cl_3N_2O_2$ | 451.77 | 4.25 | 81.5 | 2.5 |
| 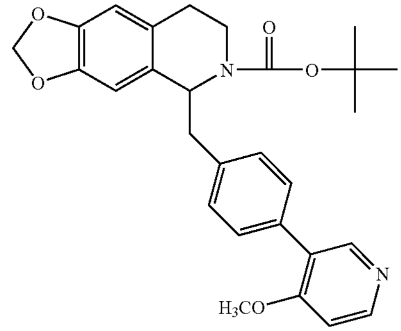 [SMILES: COc1ccncc1-c1ccc(CC2c3cc4c(cc3CCN2C(=O)OC(C)(C)C)OCO4)cc1] | $C_{28}H_{30}N_2O_5$ | 474.55 | 4.67 | 12.4 | 5.8 |

TABLE 2-continued

| STRUCTURE | Molecular Formula | Molecular Weight | Log P | EC50 μM Astrocyte | EC50 μM C6 |
|---|---|---|---|---|---|
| (structure shown) | $C_{23}H_{24}Cl_2N_2O_3$ | 410.89 | 3.56 | 8.3 | 1.3 |

The invention may be further described by means of the following non-limiting examples demonstrating the usefulness of compositions disclosed herein as agents for the destruction of cancer cells and treatment of cancer.

EXAMPLES

Screening and Dose Response Assays.

6,7-Dimethoxy-1-[4-(4-methoxypyridin-3-yl)benzyl]-1,2,3,4-tetrahydroisoquinolinehydrochloride (EDL-291) was synthesized as described herein in the laboratory of Dr. Duane D. Miller at The University of Tennessee Health Science Center. Briefly, the primary cultures of astrocytes and cultures of C6 glioma cell lines were handled identically with respect to treatment concentrations and manipulations of cells for the screening assays. The cells were trypsinized and transferred to 96-well plates at a cell density of $10^3$ cells/mm$^2$ in the wells. The cells were grown overnight in 100 μL of 10% FCS BME in a 37° C. incubator containing a humid, 5% $CO_2$ atmosphere.

EDL291 was dissolved completely to make a 100 μM stock solution and diluted to produce a series of concentrations. A 20 μL aliquot of these initial solutions was added to 180 μl of 2% FCS BME to produce the test concentration. The vehicle solution was tested as a control. Dilutions were performed such that co-solvent concentrations did not vary for a particular experiment. Immediately before treatment, the 10% FCS BME was removed from the cells and replaced with the 180 μl of the treatment medium. The cultured cells (normal primary cultures of rat brain astrocytes or C6 glioma purchased from ATCC) were incubated with test compound for 4 days. The cells were fixed with 4% paraformaldehyde, stained with 0.1% Cresylecth violet stain, and quantitated. The screening data was collected as four wells for each dose per compound (screening) or concentration (dose response curve). Also, the average growth of 8 wells with no treatment was used as a negative control for each plate (100% growth). The cells for dose response curves were grown in the same media and were handled in a similar manner as in the screening assays.

Data Analysis.

The cytotoxic character of each compound was reported as the percent survival, calculated as the average $A_{560}$ for treated cells divided by $A_{560}$ of untreated (100% control) cells, and expressed as a percentage. Values less than 100% indicate a cytostatic or cytotoxic effect. Dose response curves and EC50 values were attained via plots of percent survival vs. concentration.

Cell Cultures for Transplantation.

For studies in which C6 glioma are transplanted into the brain, a C6 cell line produced in the inventors' laboratory that caries the β-galactosidase marker was used. The cell line was transfected with the pCMVβ expression vector (Clontech, Palo Alto, Calif.) and stable transfectants were selected using G418 (GibcoBRL). The glioma cells were plated at a density of $5 \times 10^3$ cells/cm$^2$ into T-75 culture flasks. The cells were allowed to grow to confluence in BME with 10% fetal calf serum. On the day before transplantation, the cultures were rinsed with Hank's Balanced Salt Solution placed in BME with 10% rat serum (Equitech-Bio Inc., Kerrville, Tex.).

Survival Surgery.

A total of 18 male Sprague-Dawley rats (250-350 g) were deeply anesthetized with (13 mg/kg, Rompom and 87 mg/kg, Ketalar) for the surgery. The rats were monitored during the surgery to insure that they remained deeply anesthetized and unresponsive to pain. The skull was surgically exposed, a bur hole was placed in the skull and an injection cannula was lowered 5 mm below the cerebral cortex into the caudate. Approximately $5 \times 10^5$ C6 glioma cells were delivered into the brain over a 20 minute period. The injection cannula was removed and the incision was closed with surgical staples. The animal was allowed to recover and returned to the animal care facility.

The tumor was allowed to grow for three days prior to treatment. EDL-291 (40 mg/kg) was delivered by IP delivery twice a day for the next seven days. Animals were placed into one of two treatment groups: 9 rats received carrier solution only (Hanks Balanced Salt Solution, HBSS plus 10% DMSO) and 9 rats received EDL-291. During the treatment period the animal were monitored daily. After a treating the animals for 7 days, the rats were deeply anesthetized with 26 mg/kg Rompium and 174 mg/kg Ketalar and perfused through the heart with saline followed by 4% paraformaldehyde in phosphate buffer (pH 7.4). Brains were removed from the skull, post-fixed for 24 hours and then placed in a 30% sucrose solution. The brains were sectioned at 50 μM with a freezing microtome. One 1-in-5 series of sections was mounted on glass slides and stained by the Nissl method.

Tumor Size Determination.

The size of tumors in each animal was measured. The serial section from each case was photographed using a digital camera on a dissecting microscope. A scale was also photographed at the same magnification. The digital images were coded and the codes kept by one investigator. The digital images were analyzed to define the volume of the tumor using the program NIH image. This work was conducted in a blinded manner (XW). The codes were released and the data compiled and analyzed using a Student t test.

Results

In Vitro Test of EDL-291.

As an initial test of the efficacy of EDL-291 in selectively killing glioma, the inventors compared the ability of EDL-291 to kill cultured rat brain astrocytes. When the effects of EDL-291 on these normal brain astrocytes and C6 glioma were examined there was a distinct difference in the response. The C6 glioma cells were more sensitive to the effects of the EDL-291 than were the normal brain astrocytes. The normal astrocytes had an EC50 of 22.8 µM and the C6 glioma exhibited an EC50 of 0.6 µM. Thus, there was a 36-fold difference in the effect concentration of EDL-291 in killing C6 glioma relative to that dose needed to kill normal brain astrocytes. These data reveal that EDL-291 is highly selective against cultured C6 glioma relative to normal astrocytes.

In Vivo Analysis of the Effects of EDL-291

Figure 3:
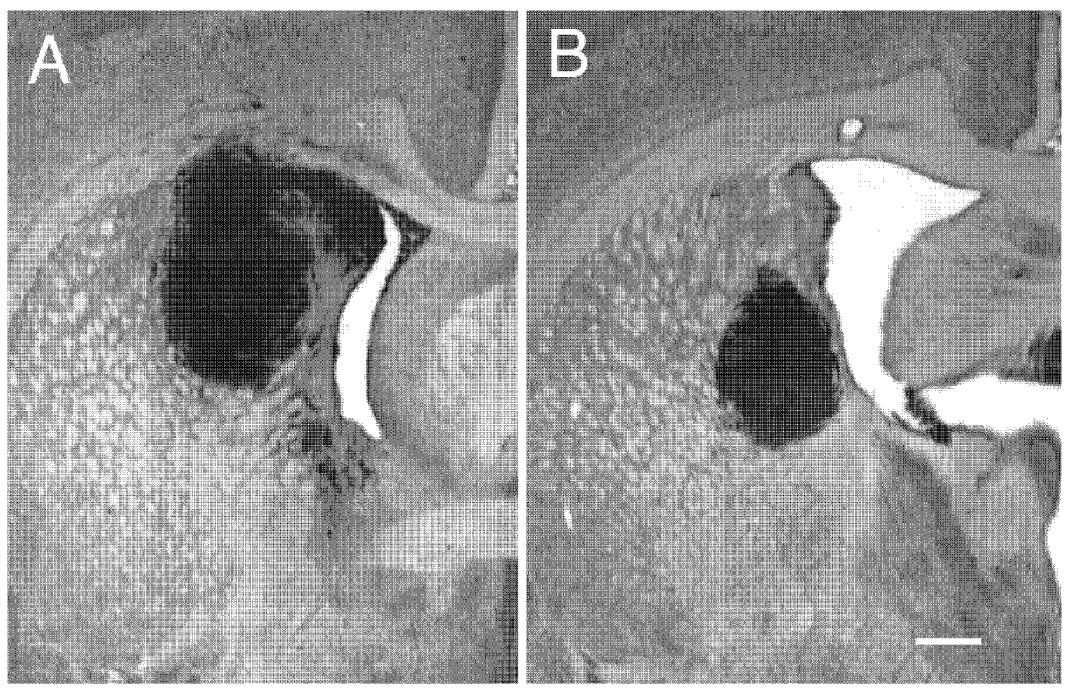
FIG. 3 shows two photomicrographs illustrating the effects of EDL-291 on the growth of transplanted C6 glioma. A is taken from an animal treated with carrier solution only and B is from an animal treated with EDL-291. In this set of experiments the tumor was implanted into the brain and allowed to establish itself for 3 days. Then the animals were treated by intraperitoneal administration of drug for 7 days. The dark blue tumor (B) in the EDL-291 treated animal is smaller than in the control animal (A). The scale bar in B is 1 mm.
Figure 4:
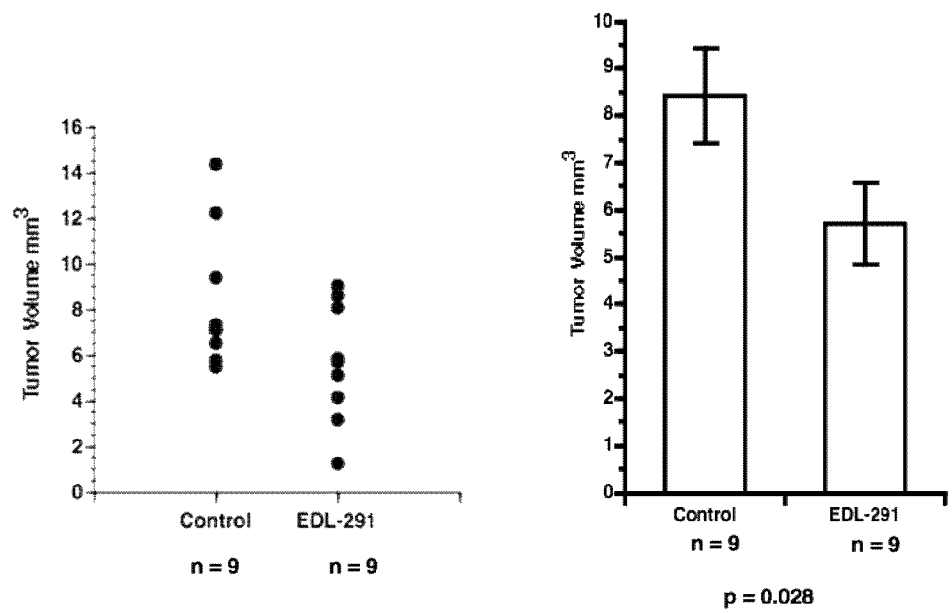
FIGS. 4a and 4b are graphs illustrating the effects of EDL-291 on tumor size. Results for individual animals are shown in 4a and the same data is shown as a mean and standard error of the mean in the bar graph in 4b. There is no evidence of acute toxicity at 40 mg/kg.

In control animals treated with the carrier solution (HBSS) relatively large tumors were observe in the brains. The C6 glioma could be observed as a large mass with cells infiltrating the surrounding tissues attached to local blood vessels. The infiltration was rather extensive with cells marking blood vessels a considerable distance away from the bulk of the tumor. A significant difference (p=0.02) in the tumor size was observed in animals treated with EDL-291. After 7 days of treatment, tumors treated with EDL-291 appeared to be smaller than those in the control animals. To provide a measure of the size of tumors in two groups, the inventors reconstructed the tumors form serial sections to define the total tumor volume in each case. The section was photographed and the area of the tumor was measured using the program NIH image. The data for all animals is shown in FIG. 3. For the rats treated with the carrier solution only (control animals) the size of the tumor ranged from 5.8 to 14.4 mm$^3$. Animals treated with EDL-291 had tumors that were smaller than those observed in the other groups. All of the other animals in the EDL-291 treatment group had tumors, however these tumors were on average smaller than those observed in the control treatment group. The size of the tumors in the EDL-291 treated animals ranged from 1.3 to 9.1 mm$^3$. This difference between the EDL-155 treated group and the control group is significant at the p=0.02 level (student t test). The tumor in one animal in the control group did not take and this animal was excluded from the data analysis.

A total of 18 male Sprague-Dawley rats (250-350 g) were deeply anesthetized with (13 mg/kg, Rompom and 87 mg/kg, Ketalar) for the surgery. The rats were monitored during the surgery to insure that they remained deeply anesthetized and unresponsive to pain. The skull was surgically exposed, a bur hole was placed in the skull and injection cannula was lowered 5 mm below the cerebral cortex into the caudate and approximately 5×10$^5$ C6 glioma cells were delivered into the brain over a 20 minute period. The injection cannula was removed and the incision was closed with surgical staples. The animal was allowed to recover and returned to the animal care facility.

Approximately three days after tumor cell implantation, animals began receiving intraperitoneal administration of EDL-291 (40 mg/kg) twice daily for the next seven days. Animals were placed into one of two treatment groups: 9 rats received vehicle only (10% DMSO in Hanks Balanced Salt Solution, HBSS) and 9 rats received EDL-291. Animals were monitored daily during the treatment period. After a survival period of eight days, the rat was deeply anesthetized with 26 mg/kg Rompom and 174 mg/kg Ketalar and perfused through the heart with saline followed by 4% paraformaldehyde in phosphate buffer (pH 7.4). Brains were removed from the skull, post-fixed for 24 hours and then placed in a 30% sucrose solution. The brains were sectioned at 50 µM with a freezing microtome. One 1-in-5 series of sections was mounted on glass slides and stained by the Nissl method.

Tumor size was measured in each animal. The serial section from each case was photographed using a digital camera on a dissecting microscope. A scale was also photographed at the same magnification. The digital images were coded and the codes kept by one inventor (Eldon E. Geisert). The digital images were analyzed to define the volume of the tumor using the program NIH image. This work was conducted in a blinded manner. The codes were released and the data compiled and analyzed using a Student t test.

Figure 2:
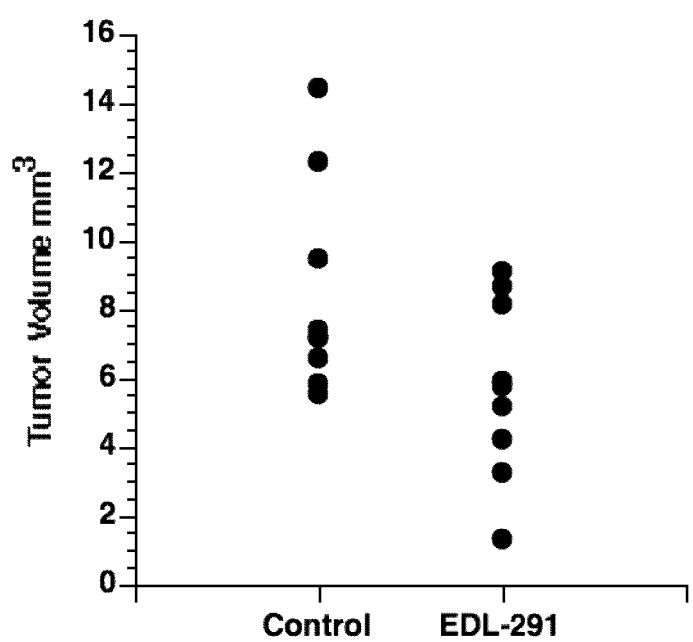
FIG. 2 is a graph indicating the volume of the C6 glioma tumor measured in each of the EDL291-treated and non-EDL291-treated animals. Animals were treated with carrier solution only (control, n=9), or with 40 mg/Kg body weight of EDL-291 (n=9) BID for 7 days. The volume of tumor was measured and is displayed in mm³. The animals treated with EDL-291 had on average 32% smaller tumors than the tumors observed in the control rats (student t test, p=0.02).

In control animals treated with the carrier solution (HBSS) relatively large tumors were observe in the brains (FIG. 1A). The C6 glioma could be observed as a large mass and out of this mass, cells were observed infiltrating the surrounding tissues attached to local blood vessels (FIG. 1B). This was rather extensive with cells marking blood vessels a considerable distance away from the bulk of the tumor. The tumors appeared to be smaller in EDL-291 treated animals compared to vehicle control animals. To provide a measure of the size of tumors in two groups, the inventors reconstructed the tumors from serial sections to define the total tumor volume in each case. The section was photographed and the area of the tumor was measured using the program NIH image. The data for all animals is shown in FIG. 2. EDL-291 treatment resulted in a statistically significant reduction in tumor size as compared to vehicle control animals.

What is claimed is:

1. A compound of Formula (I)

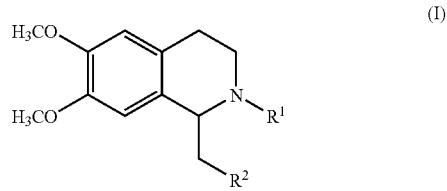

wherein R$^1$ is H, H$_2$Cl, CH$_3$, or —COOC(CH$_3$)$_3$,

R$^2$ is 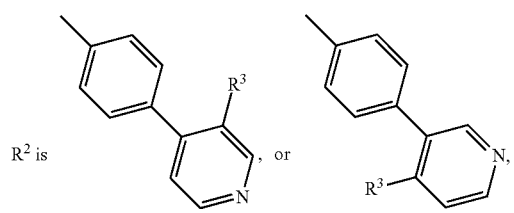

R$^3$ is —OCH$_3$, —CF$_3$, —NHSO$_2$CH$_3$, —NHCOCH$_3$, —SO$_2$CH$_3$, —N(CH$_3$)$_2$, —CN, —NO$_2$, —NH$_2$, —CO$_2$CH$_3$, —OCF$_3$, —CH$_3$, F, Cl, Br, or I.

2. A compound as in claim 1 wherein R$_2$ is

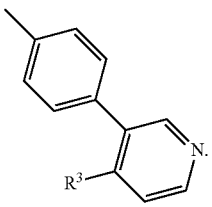

3. A compound as in claim 2 wherein $R_3$ is —OCH$_3$.

4. A compound as in claim 1 wherein $R_2$ is

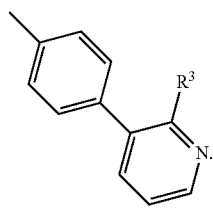

5. A compound as in claim 4 wherein $R_3$ is Cl.

6. A method of treating glioma, the method comprising administering to a subject a therapeutically effective amount of a compound as in formula (I)

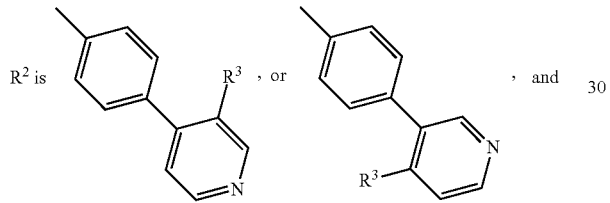
(I)

wherein $R^1$ is H, H$_2$Cl, CH$_3$, or —COOC(CH$_3$)$_3$;

$R^2$ is 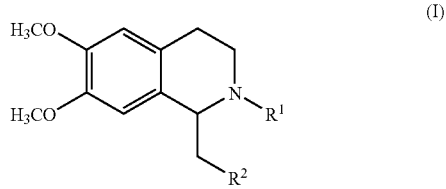, and $R^3$ is —OCH$_3$, —CF$_3$, —NHSO$_2$CH$_3$, —NHCOCH$_3$, —SO$_2$CH$_3$, —N(CH$_3$)$_2$, —CN, —NO$_2$, —NH$_2$, —CO$_2$CH$_3$, —OCF$_3$, —CH$_3$, F, Cl, Br, or I.

7. The method of claim 6 wherein $R_2$ of the compound of formula (I) is

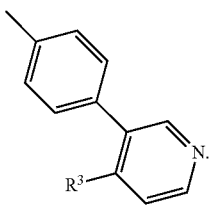

8. The method of claim 7 wherein $R_3$ of the compound of formula (I) is —OCH$_3$.

9. The method of claim 6 wherein $R_2$ of the compound of claim (I) is

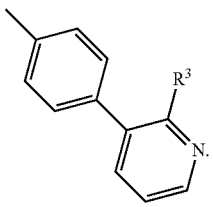

10. The method of claim 9 wherein $R_3$ of the compound of formula (I) is Cl.

* * * * *